(12) United States Patent
Rosen et al.

(10) Patent No.: US 12,115,066 B2
(45) Date of Patent: Oct. 15, 2024

(54) PROSTHETIC HEART VALVE HAVING ELONGATED SEALING MEMBER

(71) Applicant: EDWARDS LIFESCIENCES CORPORATION, Irvine, CA (US)

(72) Inventors: Izaak Rosen, Irvine, CA (US); Bich Hoang Pham, Irvine, CA (US); Timothy C. Ulrich, Irvine, CA (US); Tammy Nguyen, Irvine, CA (US); Jiangxue Han, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/370,740

(22) Filed: Sep. 20, 2023

(65) Prior Publication Data
US 2024/0008977 A1  Jan. 11, 2024

Related U.S. Application Data

(63) Continuation of application No. PCT/US2022/021337, filed on Mar. 22, 2022.
(Continued)

(51) Int. Cl.
*A61F 2/24* (2006.01)
(52) U.S. Cl.
CPC .... *A61F 2/2418* (2013.01); *A61F 2220/0075* (2013.01)
(58) Field of Classification Search
CPC .................. A61F 2/2418; A61F 2220/0075
See application file for complete search history.

(56) References Cited

U.S. PATENT DOCUMENTS 3,409,013 A  11/1968 Berry
3,548,417 A  12/1970 Kisher
(Continued)

FOREIGN PATENT DOCUMENTS

DE  0144167 C  9/1903
DE  2246526 A1  3/1973
(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.
(Continued)

*Primary Examiner* — Suzette J Gherbi
(74) *Attorney, Agent, or Firm* — Klarquist Sparkman, LLP; Joel B. German

(57) ABSTRACT

This disclosure is directed to prosthetic heart valves having elongated sealing members. As one example, a prosthetic heart valve comprises an annular frame, a leaflet assembly comprising a plurality of leaflets, and a skirt assembly comprising an inner skirt, an outer skirt, and/or a third skirt. The frame is radially compressible and expandable between a radially compressed state and a radially expanded state and comprises a plurality of apices at an inflow end. The skirt assembly forms a pocket at the inflow end of the frame that creates extra space between the inflow end of the frame and the skirt assembly when the frame is in the radially expanded state. This pocket allows the apices at the inflow end of the frame to move towards an inflow end of the pocket when the frame is radially compressed to the radially compressed state without protruding through the skirt assembly.

26 Claims, 15 Drawing Sheets

Related U.S. Application Data

(60) Provisional application No. 63/164,663, filed on Mar. 23, 2021.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |

(56) References Cited

U.S. PATENT DOCUMENTS

| | | | |
|---|---|---|---|
| 7,563,280 B2 | 7/2009 | Anderson et al. | |
| 7,585,321 B2 | 9/2009 | Cribier | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,785,366 B2 | 8/2010 | Maurer et al. | |
| 7,959,665 B2 | 6/2011 | Pienknagura | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul, Jr. et al. | |
| 8,167,932 B2 | 5/2012 | Bourang et al. | |
| 8,291,570 B2 | 10/2012 | Eidenschink et al. | |
| 8,348,998 B2 | 1/2013 | Pintor et al. | |
| 8,449,606 B2 | 5/2013 | Eliasen et al. | |
| 8,454,685 B2 | 6/2013 | Hariton et al. | |
| 8,652,203 B2 | 2/2014 | Quadri et al. | |
| 8,685,055 B2 | 4/2014 | VanTassel et al. | |
| 8,747,463 B2 | 6/2014 | Fogarty et al. | |
| 9,078,781 B2 | 7/2015 | Ryan et al. | |
| 9,974,650 B2* | 5/2018 | Nguyen-Thien-Nhon | A61F 2/2418 |
| 11,224,509 B2 | 1/2022 | Dasi et al. | |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0143390 A1 | 10/2002 | Ishii | |
| 2002/0173842 A1 | 11/2002 | Buchanan | |
| 2003/0014105 A1 | 1/2003 | Cao | |
| 2003/0040791 A1 | 2/2003 | Oktay | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0096738 A1 | 5/2005 | Cali et al. | |
| 2005/0137686 A1 | 6/2005 | Salahieh et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0021546 A1 | 1/2008 | Patz et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1 | 8/2008 | Rowe | |
| 2008/0243245 A1 | 10/2008 | Thambar et al. | |
| 2008/0255660 A1 | 10/2008 | Guyenot et al. | |
| 2008/0275537 A1 | 11/2008 | Limon | |
| 2008/0294248 A1 | 11/2008 | Yang et al. | |
| 2009/0118826 A1 | 5/2009 | Khaghani | |
| 2009/0125118 A1 | 5/2009 | Gong | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0287296 A1 | 11/2009 | Manasse | |
| 2009/0287299 A1 | 11/2009 | Tabor et al. | |
| 2009/0299452 A1 | 12/2009 | Eidenschink et al. | |
| 2009/0319037 A1 | 12/2009 | Rowe et al. | |
| 2010/0004735 A1 | 1/2010 | Yang et al. | |
| 2010/0049313 A1 | 2/2010 | Alon et al. | |
| 2010/0082094 A1 | 4/2010 | Quadri et al. | |
| 2010/0100176 A1 | 4/2010 | Elizondo et al. | |
| 2010/0168844 A1 | 7/2010 | Toomes et al. | |
| 2010/0185277 A1 | 7/2010 | Braido et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0022157 A1 | 1/2011 | Essinger et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0319991 A1 | 12/2011 | Hariton et al. | |
| 2012/0030090 A1 | 2/2012 | Johnston et al. | |
| 2012/0089223 A1 | 4/2012 | Nguyen et al. | |
| 2012/0101571 A1 | 4/2012 | Thambar et al. | |
| 2012/0123529 A1* | 5/2012 | Levi | A61F 2/2433 623/2.11 |
| 2012/0259409 A1 | 10/2012 | Nguyen et al. | |
| 2013/0023985 A1 | 1/2013 | Khairkhahan et al. | |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0296962 A1 | 10/2014 | Cartledge et al. | |
| 2014/0330372 A1 | 11/2014 | Weston et al. | |
| 2014/0343670 A1 | 11/2014 | Bakis et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2015/0135506 A1 | 5/2015 | White | |
| 2015/0157455 A1 | 6/2015 | Hoang et al. | |
| 2016/0374802 A1 | 12/2016 | Levi et al. | |
| 2017/0014229 A1* | 1/2017 | Nguyen-Thien-Nhon | A61F 2/2418 |
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |
| 2019/0159894 A1 | 5/2019 | Levi et al. | |
| 2019/0192288 A1 | 6/2019 | Levi et al. | |
| 2019/0192289 A1 | 6/2019 | Levi et al. | |
| 2021/0322163 A1* | 10/2021 | Nguyen-Thien-Nhon | A61F 2/2418 |

(56) References Cited

U.S. PATENT DOCUMENTS

| | | | |
|---|---|---|---|
| 2022/0031453 A1* | 2/2022 | Yohanan | A61F 2/2418 |
| 2022/0061986 A1* | 3/2022 | Humair | A61F 2/2427 |
| 2022/0218468 A1* | 7/2022 | Hoang | A61F 2/2412 |
| 2023/0218391 A1* | 7/2023 | Dass | A61F 2/2436 623/2.18 |
| 2023/0355378 A1* | 11/2023 | Cohen-Tzemach | A61F 2/2418 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

Bailey, S. "Percutaneous Expandable Prosthetic Valves," Textbook of Interventional Cardiology vol. 2, 2nd Ed. pp. 1268-1276. 1994.
Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.
Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.
H.R. Andersen "History of Percutaneous Aortic Valve Prosthesis," Herz No. 34. pp. 343-346. 2009.
H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Uchida, "Modifications of Gianturco Expandable Wire Stents," American Journal of Roentgenology, vol. 150. pp. 1185-1187. 1986.
Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.
Wheatley, "Valve Prostheses," Operative Surgery, 4th ed. pp. 415-424. 1986.

* cited by examiner

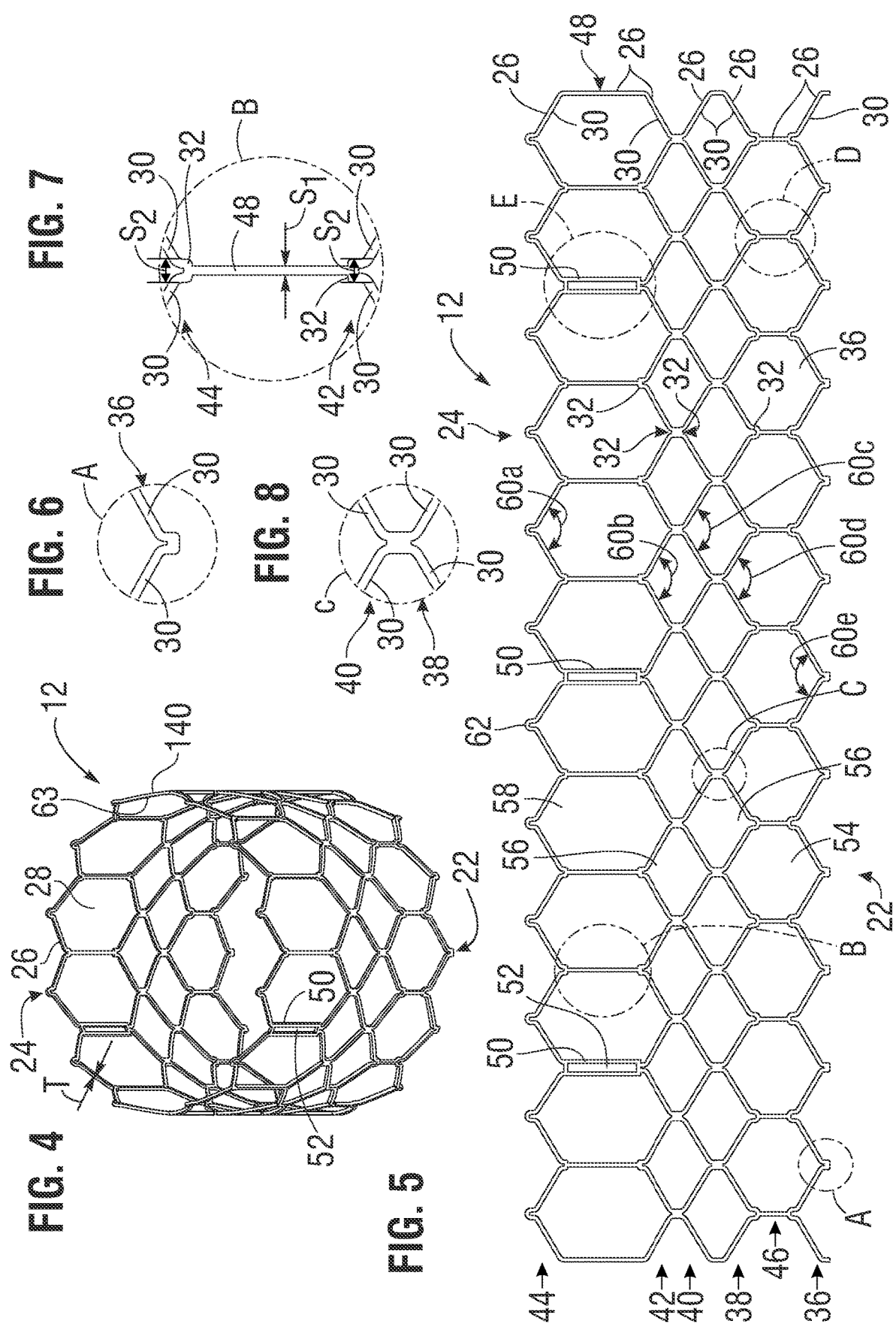

PROSTHETIC HEART VALVE HAVING ELONGATED SEALING MEMBER

CROSS-REFERENCED TO RELATED APPLICATIONS

The present application is a continuation of PCT Application No. PCT/US2022/021337, filed Mar. 22, 2022, which claims the benefit of U.S. Provisional Application No. 63/164,663, filed Mar. 23, 2021, which is incorporated herein by reference.

FIELD

The present disclosure relates to collapsible and expandable prosthetic heart valves having an elongated sealing member.

BACKGROUND

For many years, doctors attempted to repair and/or replace defective heart valves via open-heart surgery. However, because of the risks and complications of open-heart surgery, collapsible prosthetic heart valves have been developed that can be crimped to a thin enough profile (e.g., less than 8 mm in diameter) to be advanced through a patient's vasculature (e.g., veins and/or arteries) on a delivery catheter. Specifically, a physician can make a small incision near a blood vessel (e.g., a surgeon can make an incision in the patient's groin to access a femoral vein or artery) and can then advance a collapsible prosthetic heart valve in a crimped state through the patient's vasculature using a delivery catheter until the prosthetic heart valve reaches the defective native heart valve. Once at the defective native valve, the prosthetic heart valve can be expanded to its functional size via an inflatable balloon, a mechanical actuator, shape-memory materials, etc. In this way, a physician can access the heart indirectly (e.g., via a small incision in the patient's groin) without having to open the patient's chest cavity. Such transcatheter approaches are much less invasive than open heart surgery and can reduce and/or avoid the risks and complications associated with open heart surgery.

Transcatheter prosthetic heart valves typically include a radially compressible and expandable annular metal frame that supports two or more prosthetic leaflets (often made of animal (e.g., bovine) pericardial tissue) that open and close to regulate blood flow through the valve. A transcatheter prosthetic heart valve also can include an outer fabric skirt (e.g., made of polyethylene terephthalate or PET for short) that cushions and seals the rigid frame against the surrounding native heart tissue. A transcatheter prosthetic heart valve can also include an inner fabric skirt, which can be used for mounting the prosthetic leaflets to the frame and/or for sealing openings in the frame.

Some frames of transcatheter prosthetic heart valves can lengthen or elongate in the axial direction when radially compressed (such as when crimped onto a balloon of a delivery device). In some cases, elongation of the frame during crimping can cause the apices of the frame to protrude through or extend beyond one end of a skirt of the prosthetic valve. The exposed apices can contact the inner surface of an introducer sheath that is used to introduce the prosthetic valve and the delivery device into the vasculature of the patient. This can increase the push force needed to push the prosthetic valve through the introducer sheath and can deform the exposed apices, potentially damaging the valve.

Accordingly, assemblies, apparatuses, and/or methods are desired for sealing members (e.g., fabric skirts) that can protect the apices of the frame of a prosthetic heart valve during an implantation procedure.

SUMMARY

The present disclosure relates to examples of a sealing member (e.g., fabric skirt) for a prosthetic heart valve configured to protect the apices of the frame from damage caused by contact with components of a delivery system. Specifically, the present disclosure is directed to an elongated sealing member for a prosthetic heart valve that extends beyond one end of the frame of the prosthetic heart valve when the valve is not crimped (i.e., when the valve is radially expanded) to accommodate for axial lengthening of the frame during crimping. The elongated sealing member may form a pocket at one end of the frame that prevents the frame from protruding through the sealing member when the valve is crimped. Keeping the frame fully contained within the sealing member, even in its crimped state, may prevent damage to the frame and/or the rest of the valve, and/or reduce the force needed to push the valve through an introducer sheath of a delivery assembly.

In one representative example, a prosthetic heart valve comprises an annular frame, a leaflet assembly, and a skirt assembly. The annular frame comprises an inflow end and an outflow end and is radially compressible and expandable between a radially compressed state and a radially expanded state. Further, the frame comprises a plurality of apices at the inflow end. The leaflet assembly is positioned within and coupled to the frame and comprises a plurality of leaflets positioned entirely within the frame. The skirt assembly comprises an inner skirt and an outer skirt. The inner skirt extends circumferentially around an inner side of the frame and the outer skirt that extends circumferentially around an outer side of the frame. The inner and outer skirts both have respective inflow and outflow edge portions, wherein the inflow edge portions of the inner and outer skirts are stitched together such that the inflow edge portion of the inner skirt and/or the inflow edge portion of the outer skirt form(s) a pocket at the inflow end of the frame. The apices at the inflow end of the frame are disposed within the pocket and are spaced from an inflow end of the pocket when the frame is in the radially expanded state. The apices move closer to the inflow end of the pocket when the frame is radially compressed from the radially expanded state to the radially compressed state, but do not extend and/or protrude through the skirt assembly when the frame is in the radially compressed state.

In another representative example, a prosthetic heart valve comprises an annular frame, a leaflet assembly, an inner skirt, and an outer skirt. The annular frame comprises an inflow end and an outflow end and is radially compressible and expandable between a radially compressed state and a radially expanded state. Further, the frame comprises a plurality of apices at the inflow end. The leaflet assembly comprises a plurality of leaflets that are positioned within and coupled to the frame. The outer skirt extends circumferentially around an outer side of the frame and has an inflow edge portion and an outflow edge portion. The inner skirt extends circumferentially around an inner side of the frame and also has an inflow edge portion and an outflow edge portion. The inner skirt folds over itself and forms a pocket at the inflow end of the frame. The apices at the inflow end of the frame are disposed within the pocket. The pocket has an inflow end and when the frame is in the radially expanded state, the apices are spaced from the inflow end of the pocket. When the frame is radially compressed from the radially expanded state to the radially compressed state, the apices move closer to the inflow end of the pocket but do not extend and/or protrude through the inflow end of the pocket.

In yet another representative example, a prosthetic heart valve comprises an annular frame, a leaflet assembly, an inner skirt, and an outer skirt. The annular frame comprises an inflow end and an outflow end and the frame is radially compressible and expandable between a radially compressed state and a radially expanded state. Further, the frame comprises a plurality of apices at the inflow end. The leaflet assembly comprises a plurality of leaflets positioned within and coupled to the frame. The inner skirt extends circumferentially around an inner side of the frame and has an inflow edge portion and an outflow edge portion. The outer skirt extends circumferentially around an outer side of the frame and also has an inflow edge portion and an outflow edge portion. The outer skirt folds over itself and forms a pocket at the inflow end of the frame. The apices at the inflow end of the frame are disposed within the pocket. The pocket has an inflow end and when the frame is in the radially expanded state, the apices are spaced from the inflow end of the pocket. When the frame is radially compressed from the radially expanded state to the radially compressed state, the apices move closer to the inflow end of the pocket but do not extend and/or protrude through the inflow end of the pocket.

In yet another representative example, a method for assembling a prosthetic heart valve comprises: mounting an inner skirt on an inner side of a radially compressible and expandable frame that has an inflow end and an outflow end and a plurality of apices at the inflow end; mounting an outer skirt on an outer side of the frame; mounting a leaflet assembly comprising a plurality of leaflets to the frame such that the leaflet assembly is positioned entirely within the frame, between the inflow and outflow ends of the frame; stitching the inner skirt and the outer skirt together such that the inner skirt and/or the outer skirt form(s) a pocket at the inflow end of the frame or stitching a third skirt to the inner skirt and the outer skirt such that the third skirt extends beyond the inflow end of the frame and forms the pocket, wherein the plurality of apices are disposed in the pocket, and wherein the pocket has an inflow end that is separated from the plurality of apices of the frame when the frame is in a radially expanded state.

In yet another representative example, a prosthetic heart valve comprises an annular frame, a leaflet assembly, and a skirt assembly. The annular frame comprises an inflow end and an outflow end and is radially compressible and expandable between a radially compressed state and a radially expanded state. The annular frame also comprises a plurality of apices at the inflow end. The leaflet assembly is positioned within and coupled to the frame and comprises a plurality of leaflets positioned entirely within the frame. The skirt assembly comprises an inner skirt and an outer skirt. The inner skirt extends circumferentially around an inner side of the frame and has an inflow edge portion and an outflow edge portion. The outer skirt, which is separate from the inner skirt, extends circumferentially around an outer side of the frame and has an inflow edge portion and an outflow edge portion. The inflow edge portions of the inner skirt and the outer skirt are coupled to each other so as to form a pocket adjacent the inflow end of the frame, wherein the apices are disposed in the pocket, and wherein the pocket has an inflow end. When the frame is in the radially expanded state, the apices are spaced from the inflow end of the pocket and when the frame is radially compressed from the radially expanded state to the radially compressed state, the apices move closer to the inflow end of the pocket.

The foregoing and other objects, features, and advantages of the disclosed technology will become more apparent from the following detailed description, which proceeds with reference to the accompanying figures.

BRIEF DESCRIPTION OF THE DRAWINGS

FIG. 4 illustrates an elevated perspective view of a frame of the prosthetic heart valve shown in FIGS. 1-3, according to an example.

FIG. 5 illustrates a side view of the frame shown in FIG. 4 in an unfolded and flattened configuration.

FIG. 6 illustrates an enlarged view of a first portion of the frame shown in FIGS. 4-5.

FIG. 7 illustrates an enlarged view of a second portion of the frame shown in FIGS. 4-6.

FIG. 8 illustrates an enlarged view of a third portion of the frame shown in FIGS. 4-7.

DETAILED DESCRIPTION

General Considerations

Figure 1:
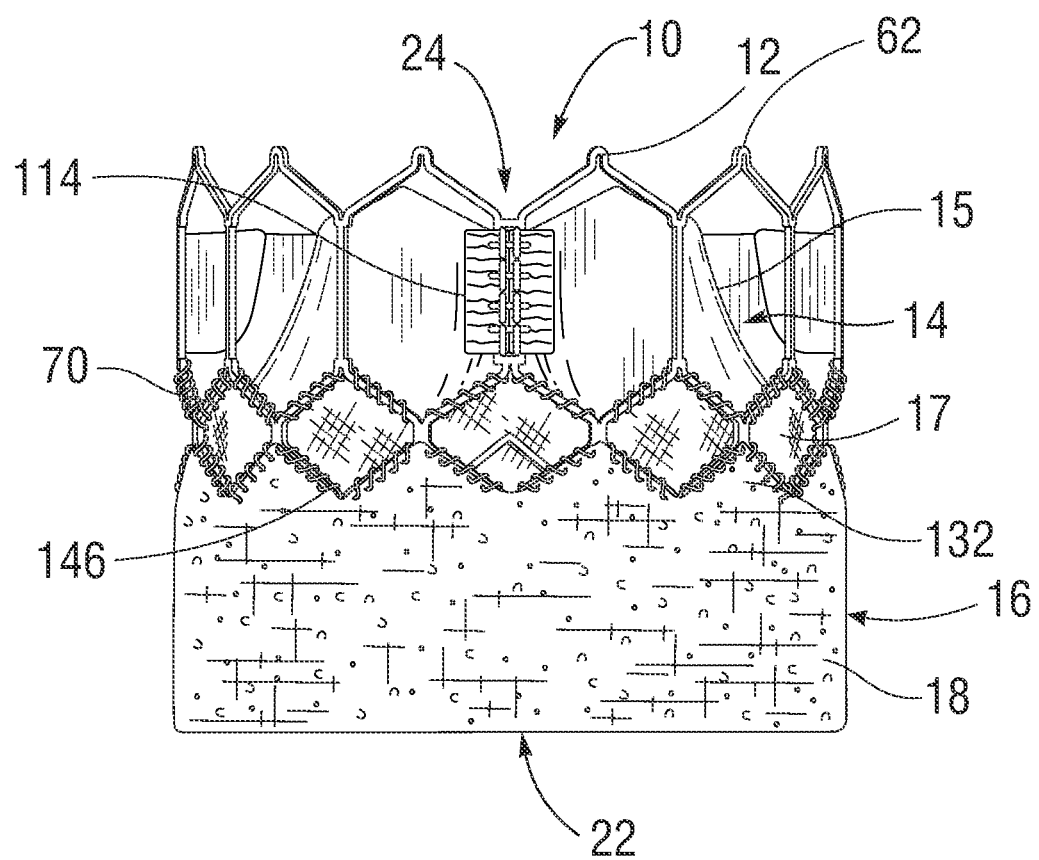
FIG. 1 illustrates a side view of a prosthetic heart valve, according to one example.

For purposes of this description, certain aspects, advantages, and novel features of the examples of this disclosure are described herein. The described methods, systems, and apparatus should not be construed as limiting in any way. Instead, the present disclosure is directed toward all novel and non-obvious features and aspects of the various disclosed examples, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, or example of the disclosure are to be understood to be applicable to any other aspect, or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing examples. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

In the context of the present application, the terms "lower" and "upper" are used interchangeably with the term's "inflow" and "outflow", respectively. Thus, for example, the lower end of the valve is its inflow end and the upper end of the valve is its outflow end.

As used herein, with reference to the prosthetic medical device (e.g., heart valve), capsule, and the delivery apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic valve).

The Disclosed Technology and Examples

Collapsible transcatheter prosthetic heart valves may be crimped to a slim profile (e.g., a radially compressed state) on a delivery apparatus so that they can be advanced through a patient's vasculature with minimal complications. However, because the frames lengthen as they are crimped, the apices of the frames can protrude through the skirt assembly and contact the inner surface of an introducer sheath that is used to introduce the prosthetic valve and the delivery device into the vasculature of the patient. This can increase the push force needed to push the prosthetic valve through the introducer sheath and can deform the exposed apices, potentially damaging the valve.

Disclosed herein are collapsible prosthetic heart valves having a sealing assembly configured to completely cover the apices of at least one end of the frame when the prosthetic valve is in a radially compressed, delivery configuration. Specifically, the prosthetic heart valves disclosed herein comprise one or more elongated sealing members (also referred to herein as "skirts") that extend past one end of the frame and form a gap or pocket (e.g., hollow space) at that end of the frame, between the sealing members and the apices of the frames. The extra space provided by this pocket allows the frames to lengthen during crimping without perforating the sealing members or allowing the apices to extend beyond the ends of the skirts. As such, the collapsible prosthetic heart valves disclosed herein can protect the apices of the frame from contacting components of a delivery system, in particular the inner surface of an introducer sheath, during an implantation procedure.

As discussed in greater detail below, the pocket can be formed by inner and/or outer skirts that are mounted on inner and outer sides, respectively, of the frame. In some examples (FIG. 23), both of the skirts may form the pocket. For example, in some such examples, the inner and outer skirts may both extend past the inflow end of the frame and may be stitched together at the pocket (below the inflow end of the frame). In other examples (FIG. 22), the pocket may be formed by the inner skirt. For example, in some such examples, the inner skirt may wrap around the inflow end of the frame, may extend over the outer skirt on the outer side of the frame, and may be stitched to the outer skirt on the outer side of the frame. In yet further examples (FIG. 24), the pocket may be formed by the outer skirt. For example, in some such examples, the skirt on the outer side of the frame may wrap around the inflow end of the frame, may extend over the inner skirt on the inner side of the frame, and may be stitched to the inner skirt on the inner side of the frame. In yet further examples (FIGS. 28 and 30-31), the pocket may be at least partially formed by a separate, third skirt that is attached to the inner skirt, the outer skirt, and/or the frame.

Additional information and examples are provided below with reference to the accompanying drawings.

Figure 2:
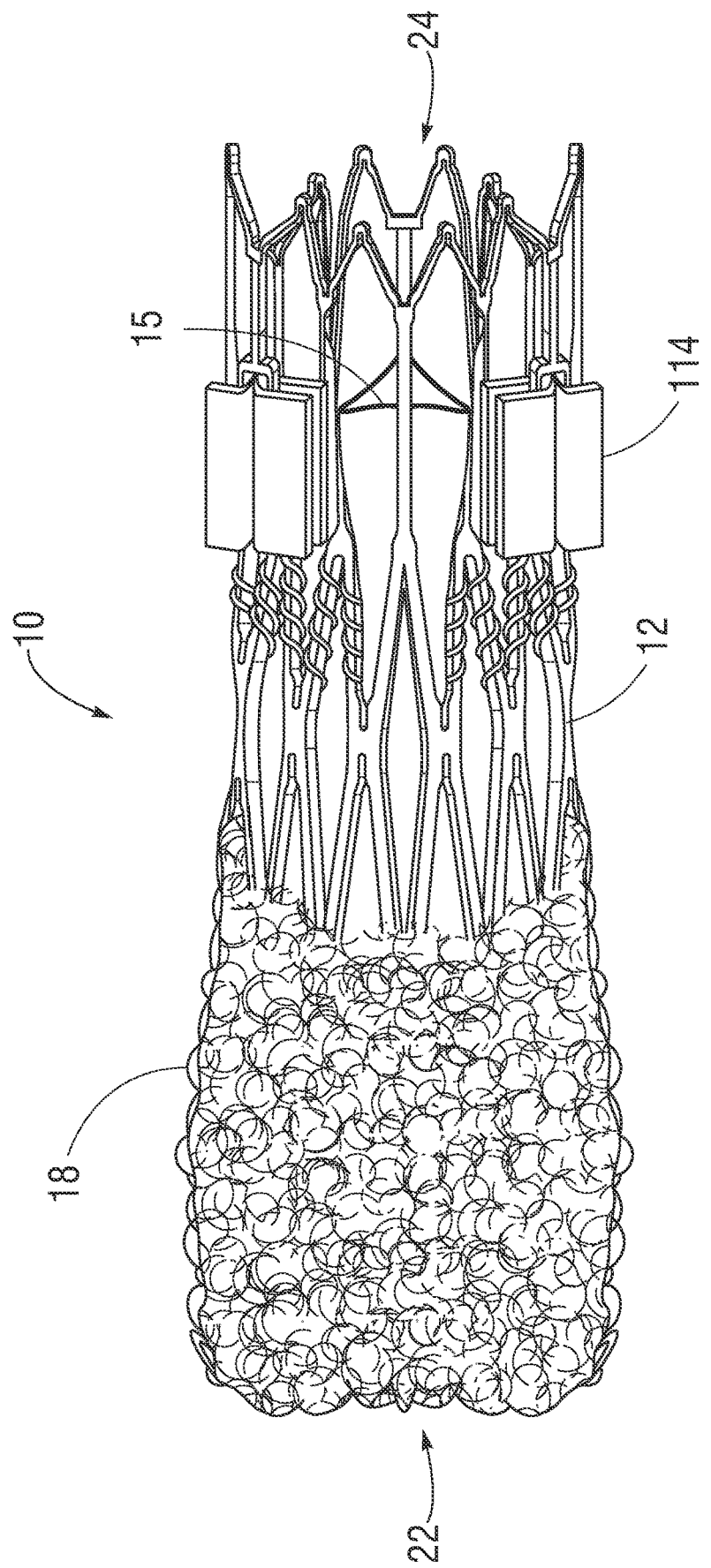
FIG. 2 illustrates an elevated perspective view of the prosthetic heart valve shown in FIG. 1 crimped on a delivery apparatus in a radially compressed state.
Figure 3:
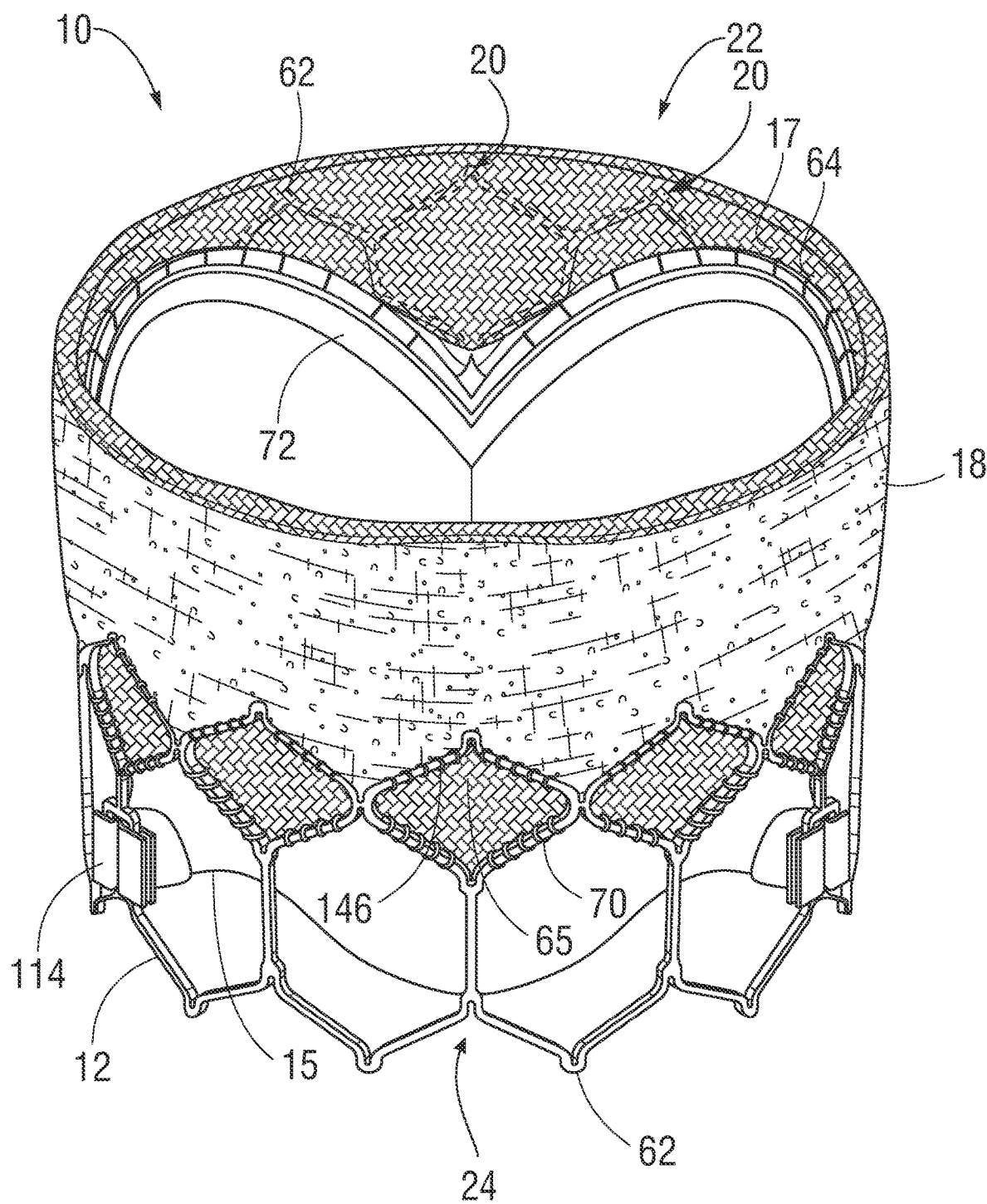
FIG. 3 illustrates an elevated perspective view of the prosthetic heart valve shown in FIGS. 1-2 in a radially expanded state.
Figure 9:
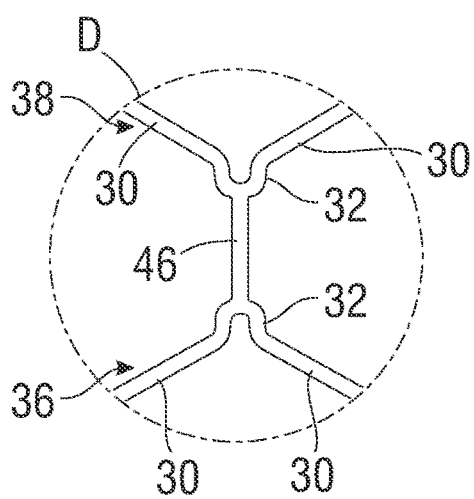
FIG. 9 illustrates an enlarged view of a fourth portion of the frame shown in FIGS. 4-8.
Figure 10:
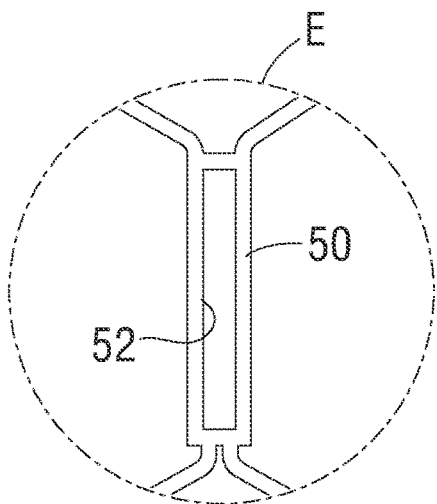
FIG. 10 illustrates an enlarged view of a fifth portion of the frame shown in FIGS. 4-9.
Figure 11:
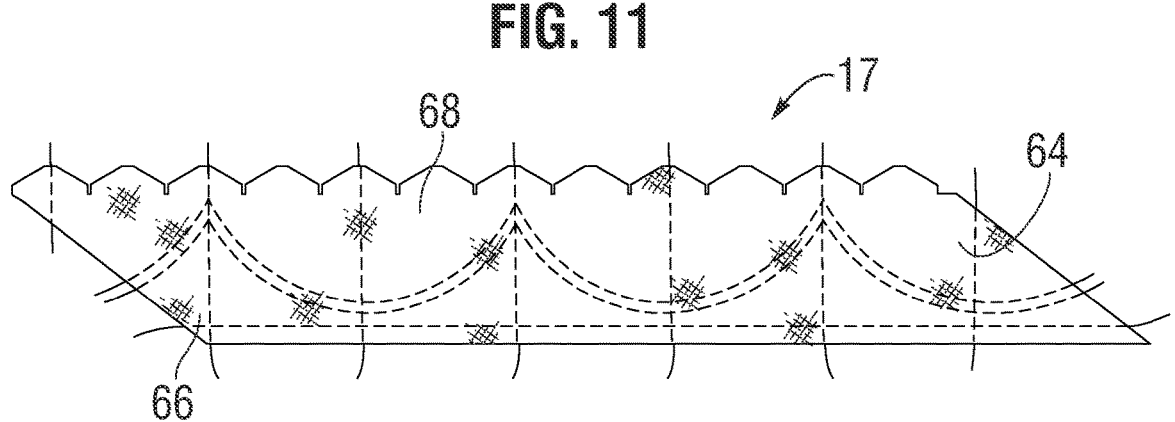
FIG. 11 illustrates a side view of an inner side of an inner skirt of the prosthetic heart valve shown in FIGS. 1-3, according to an example.
Figure 24:
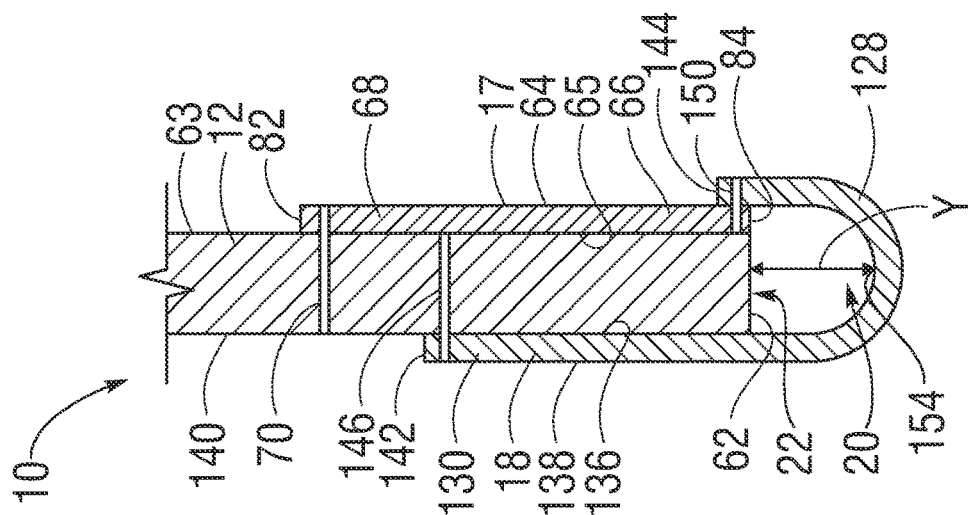
FIG. 24 illustrates a cross sectional view of an inflow edge portion of the prosthetic heart valve shown in FIGS. 1-3 in the radially expanded state shown in FIG. 3, according to an example.
Figure 23:
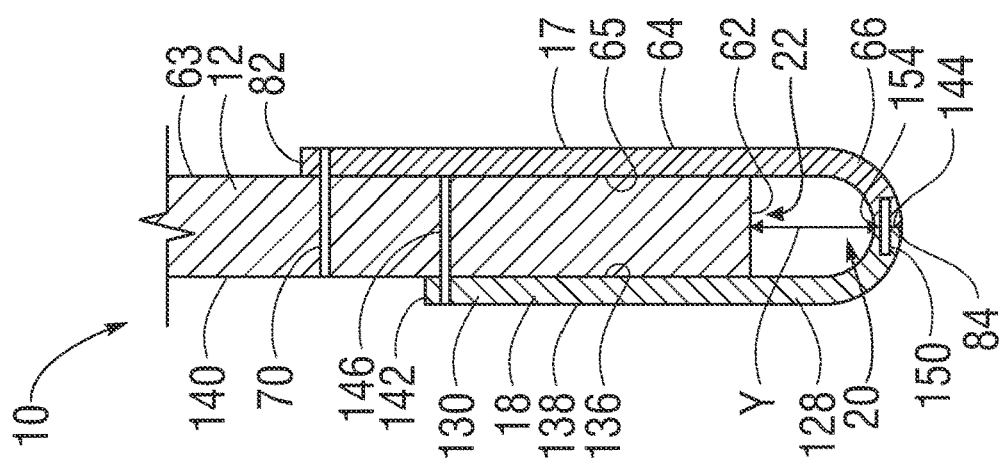
FIG. 23 illustrates a cross sectional view of an inflow edge portion of the prosthetic heart valve shown in FIGS. 1-3 in the radially expanded state shown in FIG. 3, according to an example.
Figure 25:
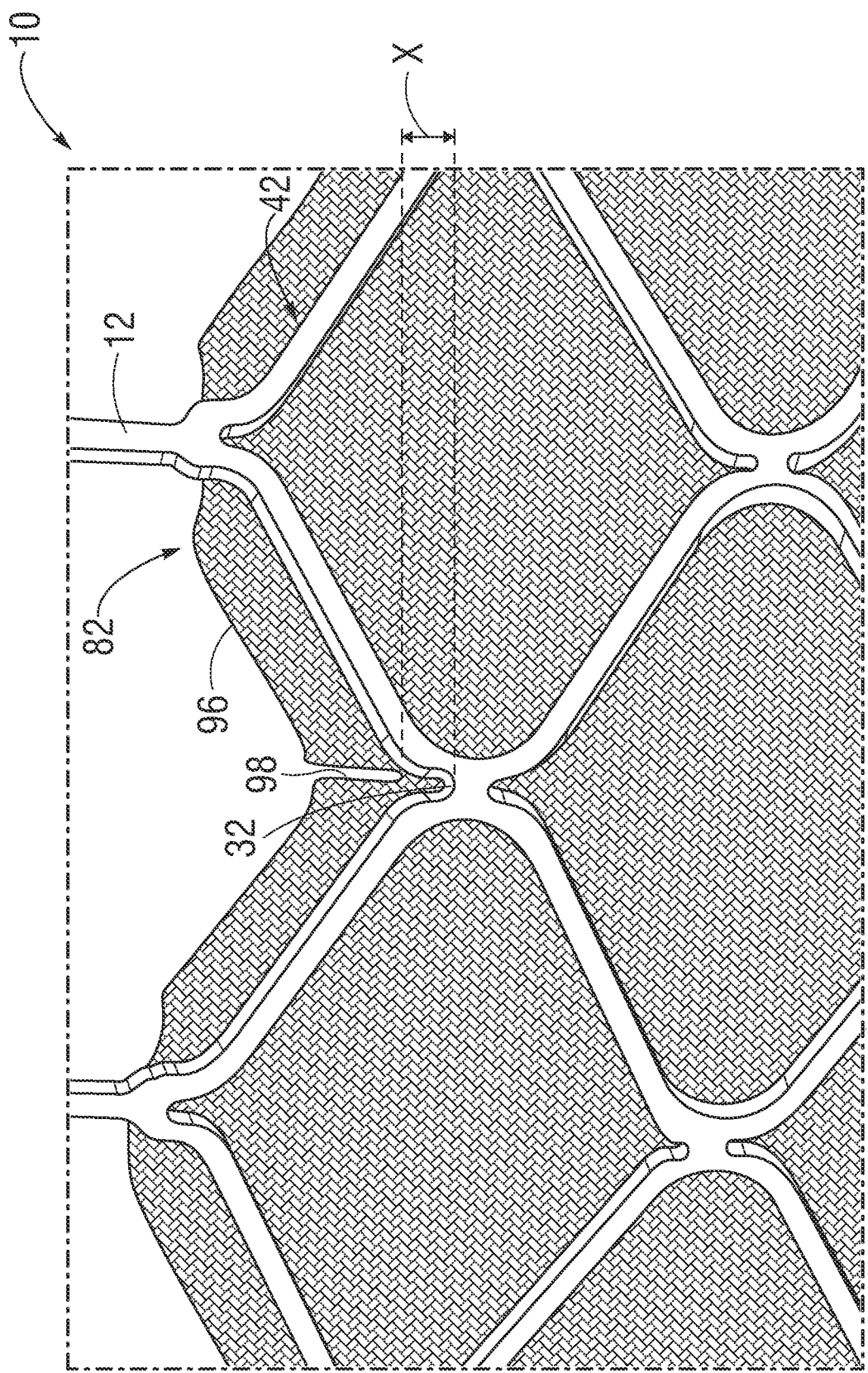
FIG. 25 illustrates an enlarged side view of a portion of the frame shown in FIGS. 4-10 where an outflow edge portion of the inner skirt shown in FIGS. 11-15 may be attached to the frame.
Figure 29:
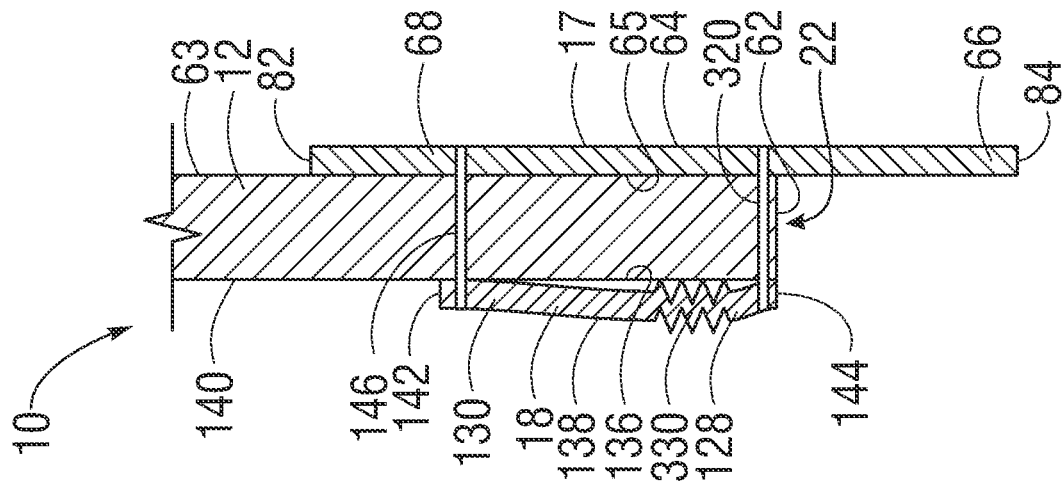
FIG. 29 illustrates a cross sectional view of an inflow edge portion of the prosthetic heart valve shown in FIGS. 1-3 in the radially expanded state shown in FIG. 3, according to an example.
Figure 30:
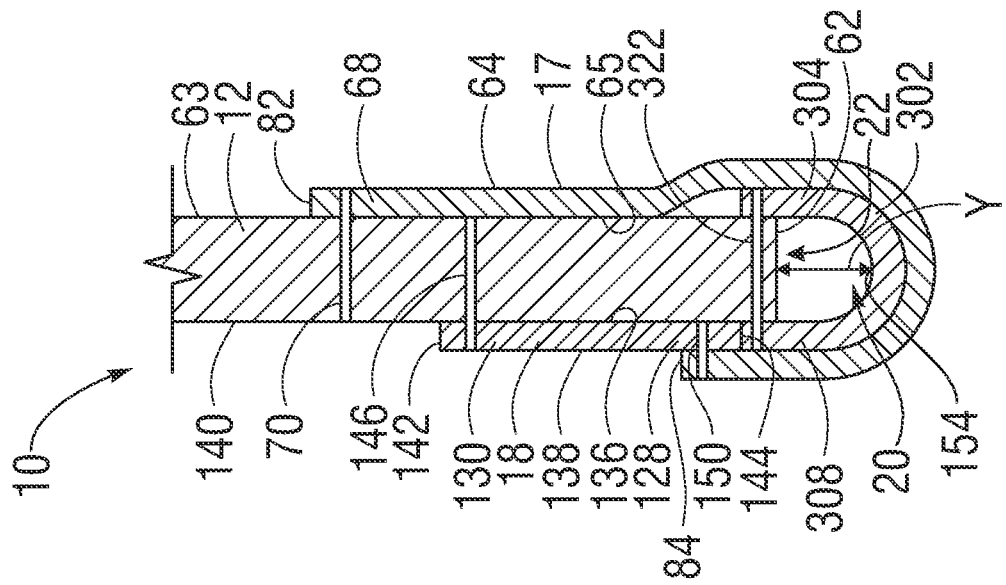
FIG. 30 illustrates a cross sectional view of an inflow edge portion of the prosthetic heart valve shown in FIGS. 1-3 in the radially expanded state shown in FIG. 3, according to an example.
Figure 31:
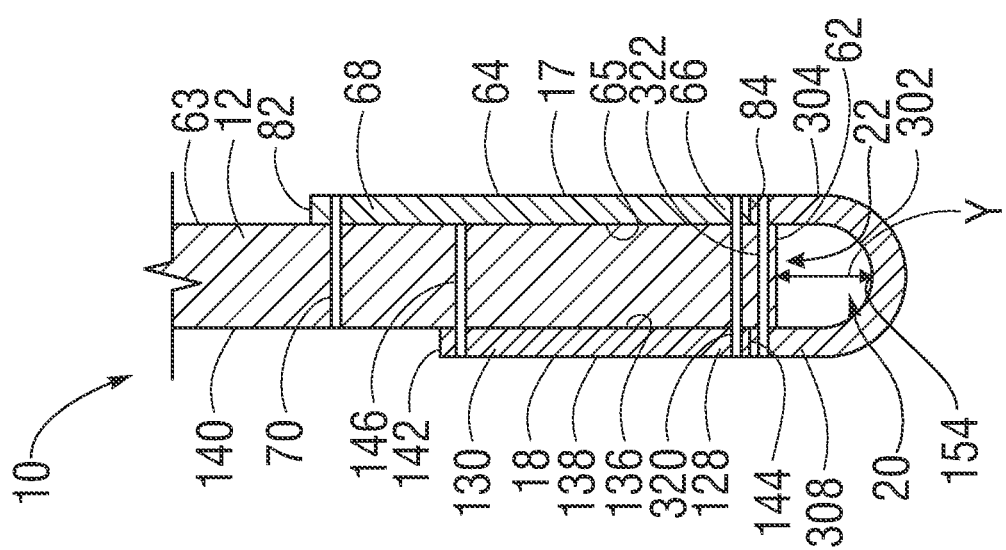
FIG. 31 illustrates a cross sectional view of an inflow edge portion of the prosthetic heart valve shown in FIGS. 1-3 in the radially expanded state shown in FIG. 3, according to an example.

FIGS. 1-31 depict various examples of prosthetic heart valves, according to the present disclosure. Specifically, FIGS. 1-3 show an exemplary prosthetic heart valve (FIGS. 1 and 3 show the valve in a radially expanded state while FIG. 2 shows the valve in a radially compressed (i.e., crimped) state), while FIGS. 4-20 and 29 depict various components of the exemplary prosthetic heart valve. Specifically, FIG. 29 depicts how the inner and outer skirts can be attached at both their inflow and outflow edge portions to the frame. FIGS. 22-24, 28, and 30-31 depict four different examples of the pocket of the exemplary prosthetic heart valve. Specifically, FIG. 22 depicts an example where the inner skirt wraps around the inflow end of the frame to form the pocket, FIG. 24 depicts an example where the outer skirt wraps around the inflow end of the frame to form the pocket, and FIG. 23 depicts an example where both the inner and outer skirt extend past the inflow end of the frame and are stitched together below the inflow end of the frame to form the pocket, and FIGS. 28 and 30-31 depict examples where a separate, third skirt is attached to the inflow edge portion of the inner skirt, the inflow edge portion of the outer skirt, and/or the inflow end of the frame to form at least a portion of the pocket. FIG. 25 depicts how the inner skirt may be aligned with the frame to ensure proper pocket length in examples where the inner skirt forms the pocket, and FIGS. 26A-27B depict how the inner and outer skirts may be stitched together in similar such examples where the inner skirt forms the pocket.

As shown in FIGS. 1-3, a prosthetic heart valve 10 (which also may be referred to herein as "transcatheter prosthetic heart valve 10," "prosthetic valve 10," and/or "radially compressible and expandable prosthetic heart valve 10") comprises an annular frame 12 that can be moved between a radially expanded and axially foreshortened state (FIGS. 1 and 3) and a radially compressed and axially elongated (i.e., crimped) state (FIG. 2), a leaflet assembly 14 comprising a plurality of leaflets 15 positioned within the frame 12, and a skirt assembly 16 (which also may be referred to herein as "sealing member assembly 16").

The skirt assembly 16 comprises an inner skirt 17 (which also may be referred to herein as "inner sealing member 17") and an outer skirt 18 (which also may be referred to herein as "outer sealing member 18") that are mounted on opposite sides of the frame 12. As introduced above, the inner skirt 17 and/or the outer skirt 18 may form a pocket 20 (FIG. 3) between the inflow end 22 of the frame 12 and the skirt assembly 16 at the inflow end 22 of the frame 12 that is configured to receive the apices of the frame 12 when the frame is crimped (i.e. radially compressed and axially elongated), such as to the radially compressed state shown in FIG. 2.

The frame 12 also comprises an outflow end 24 opposite the inflow end 22. Blood is generally configured to flow in only one direction (i.e., unidirectionally) through the valve 10, from the inflow end 22 of the frame 12 to the outflow end 24 of the frame 12. Thus, blood may be configured to enter the valve 10 at the inflow end 22 of the frame 12, to flow from the inflow end 22 of the frame 12 to the outflow end 24 of the frame 12, and then exit the frame 12 at the outflow end 24 of the frame 12.

As shown in FIGS. 4-5, the frame 12 comprises a plurality of struts 26 that form and/or otherwise define a plurality of open cells 28 (which also may be referred to herein as "openings 28"). More specifically, the plurality of struts 26 may comprise a plurality of angled struts 30 that are arranged in rows. Adjacent angled struts 30 in each row of angled struts may be directly connected to one another (i.e., without any intervening components) at junctions 32. Further, adjacent rows of angled struts 30 may be connected to one another at the junctions 32. In some examples, the junctions 32 of two or more adjacent rows of angled struts 30 may be connected directly to one another. In some examples, the junctions 32 of two or more adjacent rows of angled struts 30 may be connected to one another via one or more intermediate structures, such as one or more vertical struts (which also may be referred to herein as "axially extending struts") 34 to interconnect adjacent rows of angled struts 30.

In the example shown in FIGS. 4-5, the rows of angled struts 30 comprise five rows of angled struts 30: a first row of angled struts 36, a second row of angled struts 38, a third row of angled struts 40, a fourth row of angled struts 42, and a fifth row of angled struts 44. The first row of angled struts 36 (positioned nearest the inflow end 22 of the frame 12) may be connected to the second row of angled struts 38 via a first row of vertical struts 46, while the junctions 32 of the second row of angled struts 38 and the junctions 32 of the third row of angled struts 40 may be connected directly to one another. Similarly, the junctions 32 of the third row of angled struts 40 and the junctions 32 of the fourth row of angled struts 42 may be directly connected to one another, while the junctions 32 of the fourth row of angled struts 42 and the junctions 32 of the fifth row of angled struts 44 (positioned nearest the outflow end 24 of the frame 12) may be connected to one another via a second row of vertical struts 48 and a plurality of axially extending window frame struts 50 (which define commissure windows 52).

In this way, the plurality of struts 26 may define and/or otherwise form four rows of open cells 28. The first and second rows of angled struts 36, 38 may define and/or otherwise form a first row of open cells 54, the second, third, and fourth rows of angled struts 38, 40, 42 may form and/or otherwise define two intermediate rows of open cells 56, and the fourth and fifth rows of angled struts 42, 44 may form and/or otherwise define a fourth row of open cells 58.

As shown in FIGS. 4-5, because of the inclusion of the vertical struts 46 between the first and second rows of angled struts 36, 38 and the inclusion of the struts 48, 50 between the fourth and fifth rows of angled struts 42, 44, the cells of the first row of open cells 54 and the fourth row of open cells 58 may be larger than the cells of the two intermediate rows of open cells 56. Further, the struts 48, 50 may be longer than the vertical struts 46, and thus, the cells of the fourth row of open cells 58 may be larger than the cells of the first row of open cells 54. The relatively large size of the cells of the fourth row of open cells 58 may allow portions of the leaflet assembly 14 to protrude, or bulge, into and/or through the frame 12 when the frame 12 is crimped in order to minimize the crimping profile. In general, the geometry of the struts 26 and junctions 32 assists in making the open cells 28 large enough when the frame 12 is in the radially compressed state (FIG. 2) to allow portions of the leaflets 15 to protrude or bulge outwardly through frame 12. This allows the valve 10 to be crimped to a relatively smaller diameter than if all of the leaflet material were constrained within the crimped frame.

Further, the relatively large size of the first row of open cells 54 allows the frame, when crimped (FIG. 2), to assume an overall tapered shape that tapers from a maximum diameter at the outflow end 24 of the frame 12 to a minimum diameter at the inflow end 22. When crimped, the frame 12 has a reduced diameter region extending along a portion of the frame adjacent the inflow end 22 of the frame that generally corresponds to the region of the frame 12 covered by the outer skirt 18. In some examples, the reduced diameter region is reduced compared to the diameter of the upper portion of the frame 12 (which is not covered by the outer skirt 18) such that the outer skirt 18 does not increase the overall crimp profile of the valve 10. When the valve 10 is deployed, the frame 12 can expand from the radially compressed state (FIG. 2) to the radially expanded state (FIGS. 1, 3, 4, 15, and 20) in which the frame 12 is generally cylindrically and annularly shaped. In one example, the frame 12 of a 26-mm prosthetic valve, when crimped, has a first diameter of 14 French at the outflow end 24 of the frame 12 and a second diameter of 12 French at the inflow end 22 of the frame 12.

As best shown in FIG. 7, the struts 46, 48, and/or 50 can have a thickness 51 that is less than the thicknesses S2 of the junctions 32. The junctions 32 can help to prevent full closure of the open cells 28.

The frame 12 is configured to reduce, to prevent, or to minimize possible over-expansion of the prosthetic valve at a predetermined balloon pressure, especially at the outflow end portion of the frame, which supports the leaflet assembly 14. In one aspect, the frame 12 is configured to have relatively larger angles 60a, 60b, 60c, 60d, 60e between angled struts 30, as shown in FIG. 5. The larger the angle, the greater the force required to open (expand) the frame. As such, the angles between the angled struts 30 of the frame 12 can be selected to limit radial expansion of the frame 12 at a given opening pressure (e.g., inflation pressure of the balloon). In particular examples, these angles are at least 110 degrees or greater when the frame is expanded to its functional size, and even more particularly these angles are up to about 120 degrees when the frame is expanded to its functional size.

The frame 12 also may comprise a plurality of apices 62 at the inflow and/or outflow ends 22, 24. The apices 62 may be formed at the inflow and/or outflow ends 22, 24 by the angled struts 30. Specifically, the first row of angled struts 36 and the fifth row of angled struts 44 may form the plurality of apices 62 at the inflow end 22 and the outflow end 24, respectively, of the frame 12. The apices 62 may be formed at and/or where adjacent angled struts 30 connect.

Although the frame 12 is shown as including five rows of angled struts 30 and four rows of open cells 28 in the drawings, it should be appreciated that the frame 12 may comprise more or less than five rows of angled struts 30 and/or four rows of open cells 28 in other examples.

The frame 12 also comprises the window frame struts 50, which form and/or otherwise define the commissure windows 52 (three in the illustrated example) that are adapted to mount the commissures of the leaflet assembly 14 to the frame 12, as described in greater detail below. Each pair of window frame struts 50 is configured to mount a respective commissure of the leaflet assembly 14. As can be seen in FIGS. 4-5, each window frame strut 50 is secured at its upper and lower ends to the adjacent rows of angled struts 30 to provide a robust configuration that enhances fatigue resistance under cyclic loading of the prosthetic valve compared to known, cantilevered struts for supporting the commissures of the leaflet assembly. This configuration enables a reduction in the frame wall thickness to achieve a smaller crimped diameter of the prosthetic valve. In particular examples, the thickness T of the frame 12 (FIG. 4) measured between the inner diameter and outer diameter is about 0.48 mm or less. FIGS. 6, 7, 8, 9, and 10 are enlarged views of the portions of the frame 12 identified by letters A, B, C, D, and E, respectively, in FIG. 5.

The frame 12 can be made of any of various suitable plastically-expandable materials (e.g., stainless steel, etc.) or self-expanding materials (e.g., nickel titanium alloy (NiTi), such as nitinol) as known in the art. When constructed of a plastically-expandable material, the frame 12 (and thus the prosthetic heart valve 10) can be crimped to the radially compressed state on a delivery catheter and then expanded inside a patient by an inflatable balloon or equivalent expansion mechanism. When constructed of a self-expandable material, the frame 12 (and thus the prosthetic heart valve 10) can be crimped to the radially compressed state and restrained in the radially compressed state by insertion into a sheath or equivalent mechanism of a delivery catheter. Once inside the body, the valve 10 can be advanced from the delivery sheath, which allows the valve 10 to expand to its radially expanded state.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular examples, frame 12 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. It has been found that the use of MP35N® alloy to form frame 12 provides superior structural results over stainless steel. In particular, when MP35N® alloy is used as the frame material, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

In some examples, the frame 12 may be formed from a single piece of material. In some such examples, the open cells 28 may be formed, in some examples, by removing material from the single piece of material (e.g., via machining, milling, laser cutting, etc.). However, in other such examples, the frame 12 and the open cells 28 may be formed via a molding process (e.g., die casting, injection molding, etc.). In yet further examples, the frame 12 may be formed from two or more pieces that are formed separately and then coupled together via any suitable coupling means (e.g., welding, adhesives, fasteners, etc.).

As shown in FIGS. 1, 3, 15, and 20, the inner skirt 17 is mounted on an inner side 63 of the frame and may be coupled and/or otherwise secured to the frame 12, such as via sutures. The inner skirt 17 may comprise an inner side 64 (FIG. 11) opposite an outer side 65 (FIG. 12), with the inner side 64 facing radially inward (towards the lumen of the valve 10) and the outer side 65 facing radially outward and directly contacting the inner side 63 of the frame 12. In the example shown in FIGS. 1, 3, 15, and 20, the inner skirt 17 may be stitched to the fourth row of angled struts 42. Specifically, the inner skirt 17 may comprise an inflow edge portion 66 opposite an outflow edge portion 68, and the outflow edge portion 68 of the inner skirt 17 may be coupled to the fourth row of angled struts 42 via sutures 70. In some such examples, a plurality of projections 96 that may be formed on the outflow edge portion 68 of the inner skirt 17 may be wrapped over the fourth row of angled struts 42 and secured to the fourth row of angled struts via sutures 70. As discussed in greater detail below, during alignment and attachment of the outflow edge portion 68 of the inner skirt 17 to the fourth row of angled struts 42, a user may ensure that the outflow edge portion 68 of the inner skirt 17 does not extend more than a threshold amount X (FIG. 25) past the junctions 32 of the fourth row of angled struts 42 in order to maintain an adequate length for the pocket 20 at the inflow end 22 of the frame 12.

The main functions of the inner skirt 17 are to assist in securing the leaflet assembly 14 to the frame 12 and to assist in forming a good seal between the prosthetic valve 10 and the native annulus by blocking the flow of blood through the open cells 28 of the frame 12 below the lower edge of the leaflets 15. The inner skirt 17 desirably comprises a tough, tear resistant material such as polyethylene terephthalate (PET), although various other synthetic materials or natural materials (e.g., pericardial tissue) can be used. The thickness of the skirt desirably is less than about 0.15 mm (about 6 mil), and desirably less than about 0.1 mm (about 4 mil), and even more desirably about 0.05 mm (about 2 mil). In particular examples, the skirt 17 can have a variable thickness, for example, the skirt can be thicker at at least one of its edges than at its center. In one implementation, the skirt 17 can comprise a PET skirt having a thickness of about 0.07 mm at its edges and about 0.06 mm at its center. The thinner skirt can provide for better crimping performances while still providing good perivalvular sealing.

Figure 19:
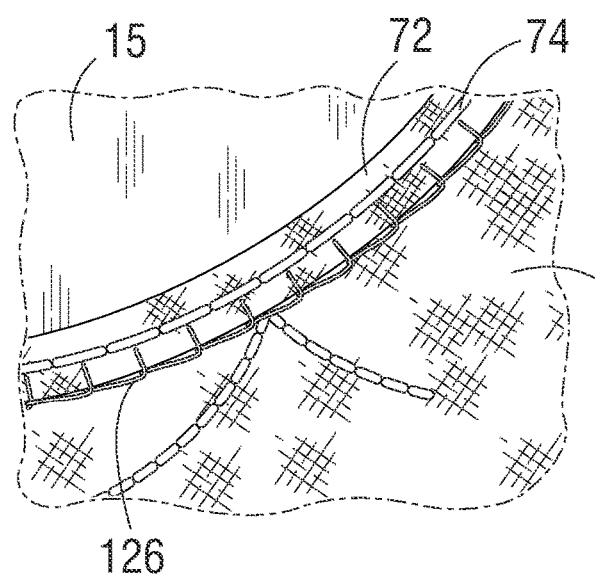
FIG. 19 illustrates a side view of a portion of a leaflet of the leaflet assembly shown in FIGS. 16-18 coupled to the inner skirt shown in FIGS. 11-15, according to an example.

Leaflet assembly 14 can be attached to the skirt via one or more reinforcing strips 72 (which collectively can form a sleeve), for example thin, PET reinforcing strips, discussed below, which enables a secure suturing and protects the pericardial tissue of the leaflet assembly from tears. Leaflet assembly 14 can be sandwiched between skirt 17 and the thin PET strips 72 as shown in FIG. 19. Sutures 74, which secure the PET strip and the leaflet assembly 14 to skirt 17, can be any suitable suture, such as Ethibond Excel® PET suture (Johnson & Johnson, New Brunswick, New Jersey). Sutures 74 desirably track the curvature of the bottom edge of leaflet assembly 14, as described in more detail below.

Figure 12:
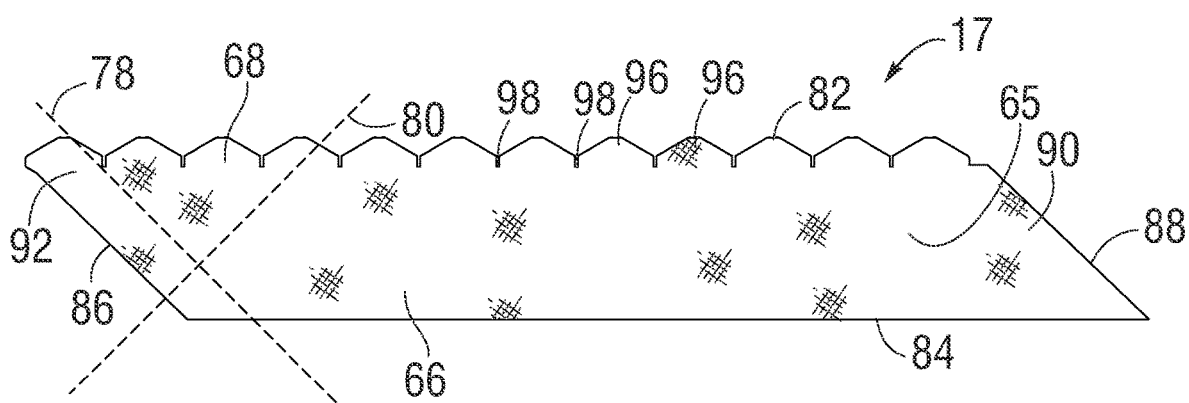
FIG. 12 illustrates a side view of an outer side of the inner skirt shown in FIG. 11.

Referring to FIG. 12, in contrast to known fabric skirts, the skirt 17 desirably is woven from a first set of fibers, or yarns or strands, 78 and a second set of fibers, or yarns or strands, 80, both of which are non-perpendicular to an outflow end 82 and an inflow end 84 of the skirt. In particular examples, the first set of fibers 78 and the second set of fibers 80 extend at angles of about 45 degrees (e.g., 15-75 degrees or 30-60 degrees) relative to the outflow and inflow ends 82, 84. For example, the skirt 17 can be formed by weaving the fibers at 45 degree angles relative to the outflow and inflow ends of the fabric. Alternatively, the skirt 17 can be diagonally cut (cut on a bias) from a vertically woven fabric (where the fibers extend perpendicularly to the edges of the material) such that the fibers extend at 45-degree angles relative to the cut outflow and inflow ends of the skirt. As further shown in FIG. 12, the opposing short edges 86, 88 of the skirt 17 desirably are non-perpendicular to the outflow and inflow ends 82, 84. For example, the short edges 86, 88 desirably extend at angles of about 45 degrees relative to the outflow and inflow ends and therefore are aligned with the first set of fibers 78. Therefore the overall general shape of the skirt 17 is that of a rhomboid or parallelogram.

Figure 13:
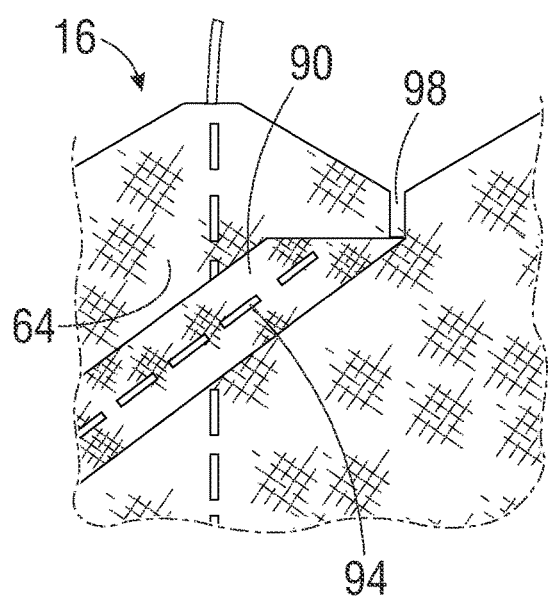
FIG. 13 illustrates an enlarged view of a portion of the inner skirt shown in FIGS. 11-12.
Figure 14:
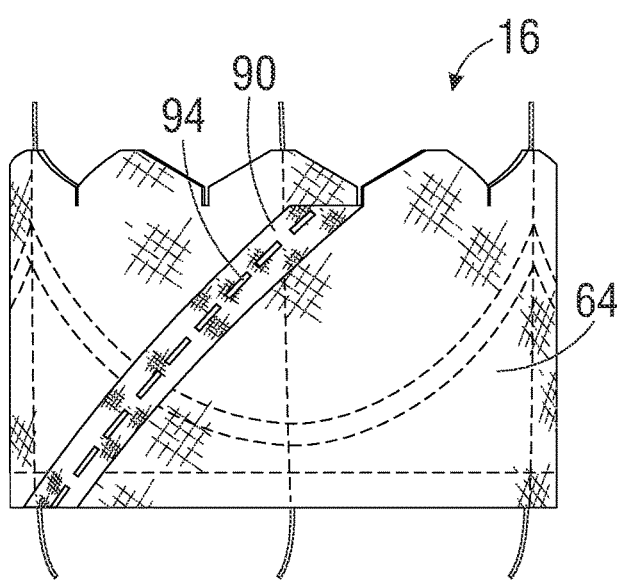
FIG. 14 illustrates an enlarged view of a portion of the inner skirt shown in FIGS. 11-13.
Figure 15:
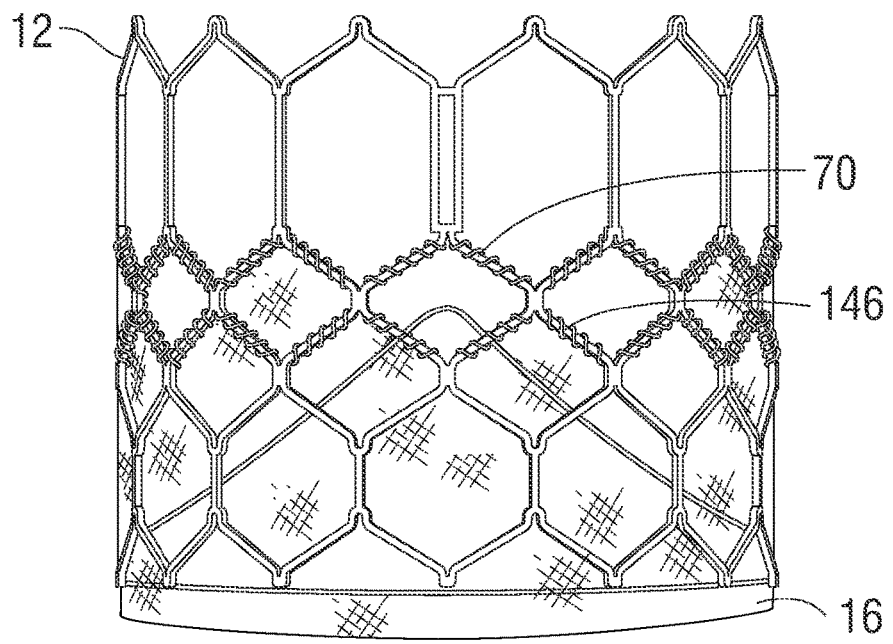
FIG. 15 illustrates a side view of the inner skirt shown in FIGS. 11-14 coupled to the frame shown in FIGS. 4-10, according to an example.

FIGS. 13 and 14 show the inner skirt 17 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The inflow edge portion 66 of the inner skirt 17 can be formed with a plurality of projections 96 that define an undulating shape that generally follows the shape or contour of the fourth row of angled struts 42 immediately adjacent the lower ends of vertical struts 48. In this manner, as best shown in FIG. 15, the outflow end 82 of the inner skirt 17 can be tightly secured to the fourth row of angled struts 42 via the sutures 70. The inner skirt 17 can also be formed with slits 98 to facilitate attachment of the skirt 17 to the frame 12. Slits 98 are dimensioned so as to allow outflow edge portion 68 of the inner skirt 17 to be partially wrapped around the fourth row of angled struts 42 and to reduce stresses in the skirt during the attachment procedure. For example, in the illustrated example, the inner skirt 17 is placed on the inner side 63 of the frame 12 and the outflow edge portion 68 of the skirt 17 is wrapped around the upper surfaces of the fourth row of angled struts 42 and secured in place with sutures 70. Wrapping the outflow edge portion 68 of the inner skirt 17 around the fourth row of angled struts 42 in this manner provides for a stronger and more durable attachment of the skirt 17 to the frame 12. The inner skirt 17 can additionally or alternatively be secured to the first, second, and/or third rows of angled struts 36, 38, 40, respectively, with sutures 70.

As shown in FIG. 25, the slits 98 may be circumferentially aligned with the junctions 32 between adjacent angled struts. In some examples, the slits 98 may not be spaced axially away from the junctions 32 by more than a threshold amount X to ensure that the pocket 20 is formed at the inflow end 22 of the frame 12 and/or to prevent overwrapping of the inner skirt 17. For example, the slits 98 may be spaced axially away from the junctions 32 (towards the outflow end 24 of the frame) of the fourth row of angled struts 42 by (i.e., the threshold amount X may be) at most 0.3 mm, 0.4 mm, 0.5 mm, 0.6 mm, 0.7 mm, 0.8 mm, 0.9 mm, and/or at most 1.0 mm. Thus, in some examples, the inflow end 84 of the inner skirt 17 may extend past (i.e., below), the apices 62 at the inflow end 22 of the frame 12. However, in other examples, the inflow end 84 of the inner skirt 17 may extend to, but not past the apices 62 at the inflow end of the frame 12. In still further examples, the inflow end 84 of the inner skirt 17 may not extend to the apices 62 at the inflow end 22 of the frame 12 and may stop short of the apices 62 at the inflow end of the frame 12.

Due to the angled orientation of the fibers relative to the inflow and outflow ends of the skirt 17, the skirt 17 can undergo greater elongation in the axial direction (i.e., in a direction from the outflow end 82 to the inflow end 84). Thus, when the frame 12 is crimped, the inner skirt 17 can elongate in the axial direction along with the frame and therefore provide a more uniform and predictable crimping profile. Each cell of the metal frame in the illustrated example includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET inner skirt 17 formed from 20-denier yarn, the yarn density can be about 15% to about 30% lower than in a typical PET skirt. In some examples, the yarn spacing of the inner skirt 17 can be from about 60 yarns per cm (about 155 yarns per inch) to about 70 yarns per cm (about 180 yarns per inch), such as about 63 yarns per cm (about 128 yarns per inch), whereas in a typical PET skirt the yarn spacing can be from about 85 yarns per cm (about 217 yarns per inch) to about 97 yarns per cm (about 247 yarns per inch). The short edges 86, 88 promote a uniform and even distribution of the fabric material along inner circumference of the frame during crimping so as to reduce or minimize bunching of the fabric to facilitate uniform crimping to the smallest possible diameter. Additionally, cutting diagonal sutures in a vertical manner may leave loose fringes along the cut edges. The short edges 86, 88 help minimize this from occurring. Compared to the construction of a typical skirt (fibers running perpendicularly to the outflow and inflow ends of the skirt), the construction of the inner skirt 17 avoids undesirable deformation of the frame struts and provides more uniform crimping of the frame.

In alternative examples, the skirt 17 can be formed from woven elastic fibers that can stretch in the axial direction during crimping of the prosthetic valve 10. The warp and weft fibers can run perpendicularly and parallel to the outflow and inflow ends of the skirt 17, or alternatively, they can extend at angles between 0 and 90 degrees relative to the outflow and inflow ends of the skirt 17, as described above.

The inner skirt 17 can be sutured to the frame 12 at locations away from the sutures 74 so that the skirt can be more pliable in that area. This configuration can avoid stress concentrations at the sutures 74, which attaches the lower edges of the leaflets to the inner skirt 17.

As noted above, the leaflet assembly 14 in the illustrated example includes three flexible leaflets 15 (although a greater or a smaller number of leaflets can be used). Additional information regarding the leaflets, as well as additional information regarding skirt material, can be found, for example, in U.S. Pat. No. 10,195,025, issued Feb. 5, 2019, which is incorporated herein by reference.

Figure 16:
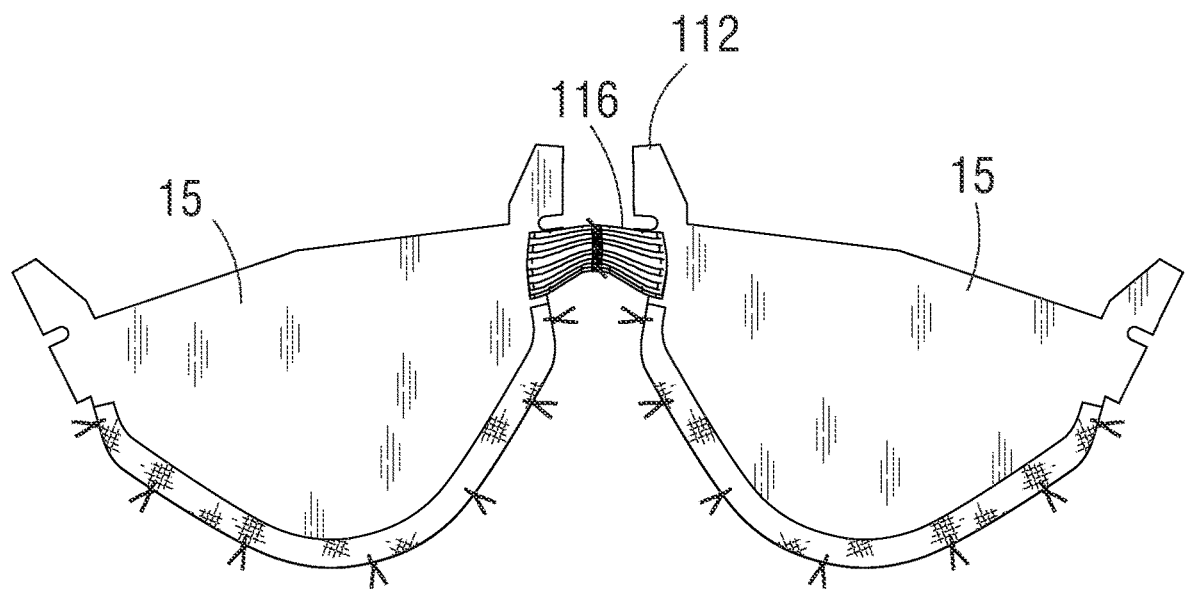
FIG. 16 illustrates a top view of adjacent leaflets of a leaflet assembly of the prosthetic heart valve shown in FIGS. 1-3 coupled to one another via a connector, according to an example.
Figure 17:
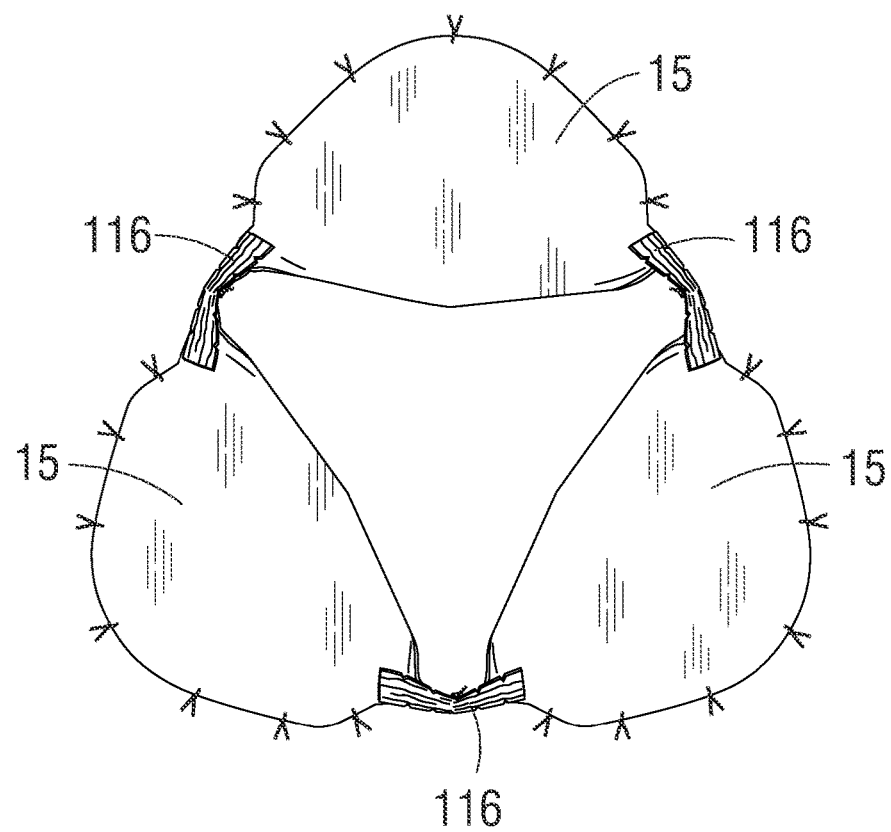
FIG. 17 illustrates a top view of the leaflet assembly shown in FIG. 16.
Figure 20:
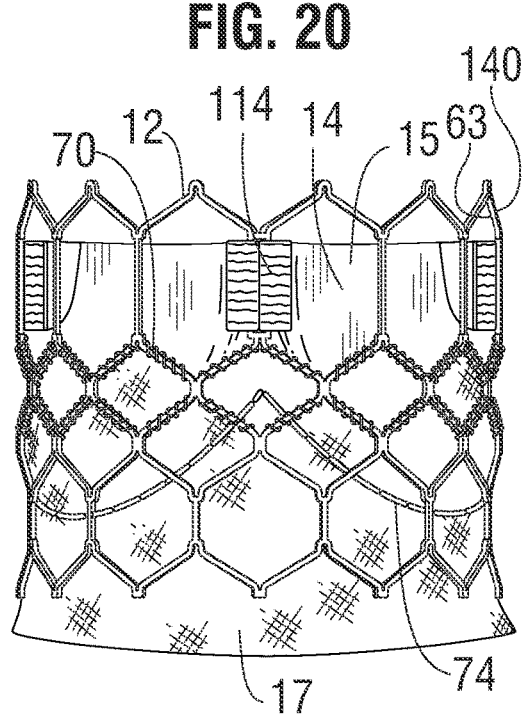
FIG. 20 illustrates a side view of the inner skirt shown in FIGS. 11-15 and the leaflet assembly shown in FIGS. 16-19 coupled to the frame shown in FIGS. 4-10, according to an example.

The leaflets 15 can be secured to one another at their adjacent sides to form commissures 114 of the leaflet assembly (FIG. 20). A plurality of flexible connectors 116 (one of which is shown in FIG. 16) can be used to interconnect pairs of adjacent sides of the leaflets and to mount the leaflets to the window frame struts 50 (FIG. 5). FIG. 16 shows the adjacent sides of two leaflets 15 interconnected by a flexible connector 116. Three leaflets 15 can be secured to each other side-to-side using three flexible connectors 116, as shown in FIG. 17. Additional information regarding connecting the leaflets to each other, as well as assembling the leaflets and the skirts to the frame, can be found, for example, in U.S. Patent Application Publication Nos. 2012/0123529 and 2019/0365530, which are incorporated herein by reference.

To protect against over-expansion of the leaflet assembly 14, the leaflet assembly 14 desirably is secured to the frame 12 below the fifth row of angled struts 44, as best shown in FIG. 1. Specifically, the inflow and outflow ends 22, 24 of the frame 12 may generally tend to over-expand more so than the middle portion of the frame 12 due to the "dog-boning" effect of the balloon used to expand the prosthetic valve 10. Thus, in the event that the outflow end 24 of the frame 12 is over-expanded, the leaflet assembly 14 is positioned at a level below where over-expansion is likely to occur, thereby protecting the leaflet assembly 14 from over-expansion.

Another benefit of mounting the leaflets 15 at a location spaced away from the outflow end 24 of the frame 12 is that when the prosthetic valve 10 is crimped on a delivery catheter, the outflow end 24 of the frame 12 rather than the leaflets 15 is the proximal-most component of the prosthetic valve 10. As such, if the delivery catheter includes a pushing mechanism or stop member that pushes against or abuts the outflow end 24 of the prosthetic valve 10, the pushing mechanism or stop member contacts the outflow end 24 of the frame 12, and not leaflets 15, so as to avoid damage to the leaflets 15.

As noted above, the inner skirt 17 can be used to assist in suturing the leaflet assembly 14 to the frame 12. The inner skirt 17 can have an undulating temporary marking suture to guide the attachment of the lower edges of each leaflet 15. The inner skirt 17 itself can be sutured to the struts of the frame 12 using sutures 70, as noted above, before securing the leaflet assembly 14 to the skirt 17. The struts that intersect the marking suture desirably are not attached to the inner skirt 17. This allows the inner skirt 17 to be more pliable in the areas not secured to the frame and minimizes stress concentrations along the suture line that secures the lower edges of the leaflets to the skirt. As noted above, when the skirt is secured to the frame, the fibers 78, 80 of the skirt (see FIG. 12) generally align with the angled struts of the frame to promote uniform crimping and expansion of the frame.

Figure 18:
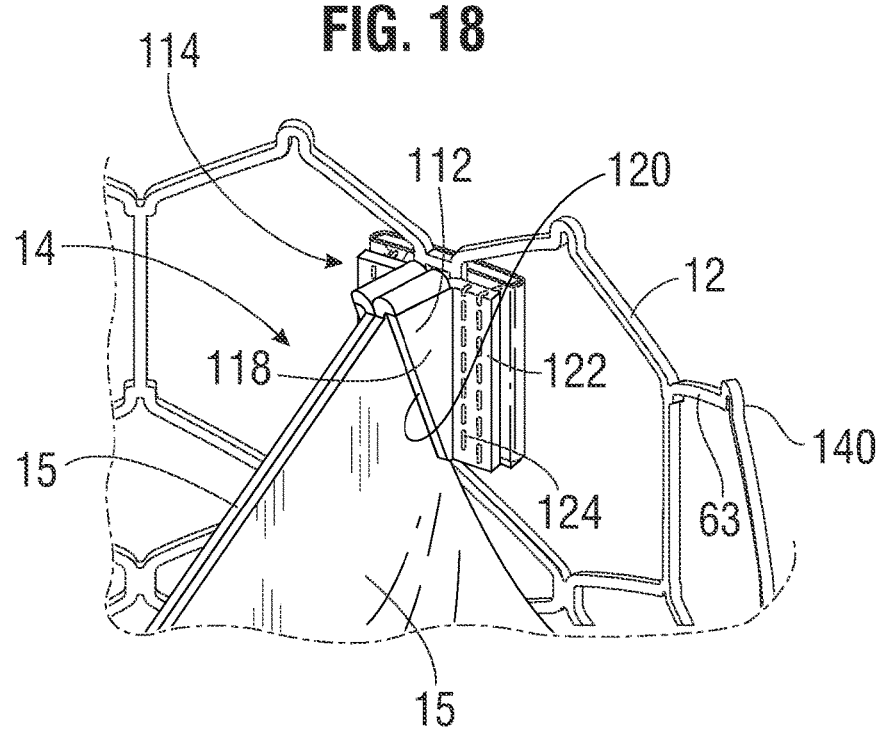
FIG. 18 illustrates an elevated perspective view of a commissure of the leaflet assembly shown in FIGS. 16-17 coupled to the frame shown in FIGS. 4-10, according to an example.

FIG. 18 shows one specific approach for securing the commissures 114 of the leaflet assembly 14 to the commissure window frame struts 50 of the frame 12. The flexible connector 116 (FIG. 17) securing two adjacent sides of two leaflets 15 is folded widthwise and the upper tab portions 112 are folded downwardly against the flexible connector. Each upper tab portion 112 is creased lengthwise (vertically) to assume an L-shape having an inner portion 118 folded against the inner surface of the leaflet 15 and an outer portion 122 folded against the connector 116. The outer portion 122 can then be sutured to the connector 116 along a suture line 124. Next, the commissure tab assembly is inserted through the commissure window 52 of a corresponding pair of window frame struts 50, and the folds outside of the window frame struts 50 can be sutured to portions 122.

FIG. 18 also shows that the folded down upper tab portions 112 can form a double layer of leaflet material at the commissures. The inner portions 118 of the upper tab portions 112 are positioned flat against layers of the two leaflets 15 forming the commissures, such that each commissure comprises four layers of leaflet material just inside of the window frame struts 50. This four-layered portion of the commissures can be more resistant to bending, or articulating, than the portion of the leaflets 15 just radially inward from the relatively more-rigid four-layered portion. This causes the leaflets 15 to articulate primarily at inner edges 120 of the folded-down inner portions 118 in response to blood flowing through the prosthetic valve during operation within the body, as opposed to articulating about or proximal to the axial struts of the window frame struts 50. Because the leaflets articulate at a location spaced radially inwardly from the window frame struts 50, the leaflets 15 can avoid contact with and damage from the frame 12. However, under high forces, the four layered portions of the commissures can splay apart about a longitudinal axis adjacent to the window frame struts 50, with each inner portion 118 folding out against the respective outer portion 122. For example, this can occur when the prosthetic valve 10 is compressed and mounted onto a delivery shaft, allowing for a smaller crimped diameter. The four-layered portion of the commissures can also splay apart about the longitudinal axis when the balloon catheter is inflated during expansion of the prosthetic valve, which can relieve some of the pressure on the commissures caused by the balloon, reducing potential damage to the commissures during expansion.

After all three commissure tab assemblies are secured to respective window frame struts 50, the lower edges of the leaflets 15 between the commissure tab assemblies can be sutured to the inner skirt 17. For example, as shown in FIG. 19, each leaflet 15 can be sutured to the inner skirt 17 via sutures 74 using, for example, Ethibond Excel® PET thread. The sutures 74 can be in-and-out sutures extending through each leaflet 15, the inner skirt 17, and each reinforcing strip 72. Each leaflet 15 and respective reinforcing strip 72 can be sewn separately to the inner skirt 17. In this manner, the lower edges of the leaflets 15 are secured to the frame 12 via the inner skirt 17. As shown in FIG. 19, the leaflets can be further secured to the skirt with blanket sutures 126 that extend through each reinforcing strip 72, leaflet 15 and the inner skirt 17 while looping around the edges of the reinforcing strips 72 and leaflets 15. The blanket sutures 126 can be formed from PTFE suture material. FIG. 20 shows a side view of the frame 12, leaflet assembly 14 and the inner skirt 17 after securing the leaflet assembly 14 and the inner skirt 17 to the frame 12 and the leaflet assembly 14 to the inner skirt 17.

In some examples (e.g., FIGS. 3 and 20), the leaflet assembly 14, including the leaflets 15, are positioned entirely within the frame 12 (between the inflow and outflow ends 22, 24 of the frame 12) and do not extend past the inflow end 22 of the frame 12. In some such examples, the leaflets 15 do not extend to the inflow end 22 of the frame 12 and instead stop short of the inflow end 22 of the frame 12. For example, as shown in FIG. 3, the leaflets 15 do not extend to the apices 62 at the inflow end 22 of the frame 12. Thus, the leaflet assembly 14 may be shorter than the frame 12 and may be positioned entirely within the frame 12, such that the leaflets 15 do not extend past the inflow and outflow ends 22, 24 of the frame 12.

Figure 21:
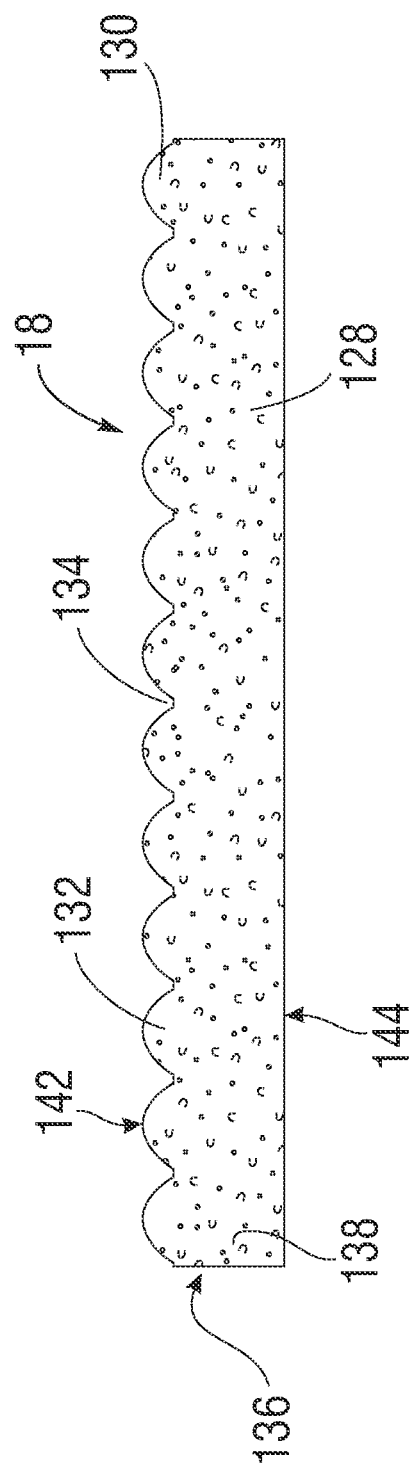
FIG. 21 illustrates a side view of an outer skirt of the prosthetic heart valve shown in FIGS. 1-3, according to an example.
Figure 22:
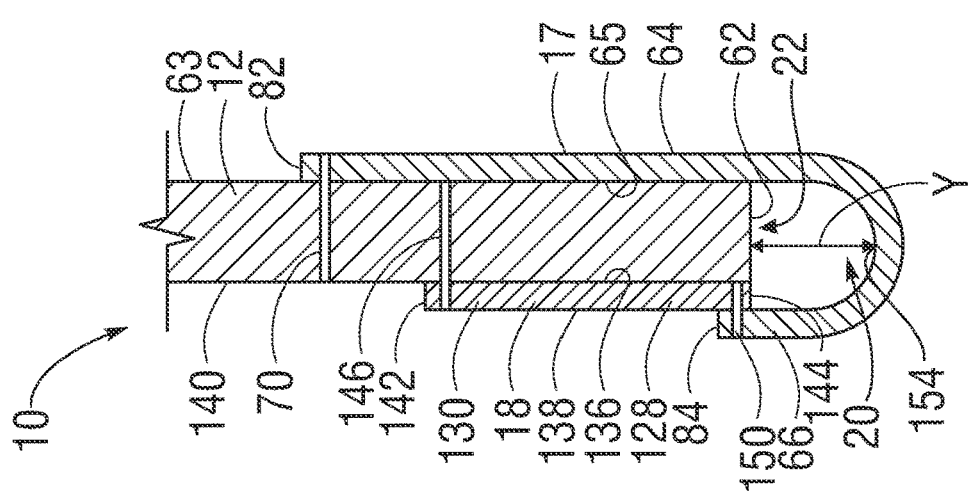
FIG. 22 illustrates a cross sectional view of an inflow edge portion of the prosthetic heart valve shown in FIGS. 1-3 in the radially expanded state shown in FIG. 3, according to an example.

FIG. 21 is a flattened view of the outer skirt 18 prior to its attachment to the frame 12. The outer skirt 18 can be laser cut or otherwise formed from a strong, durable material such as PET or various other suitable synthetic or natural materials configured to restrict and/or prevent blood-flow therethrough. The outer skirt 18 can comprise a substantially straight lower (inflow or upstream) edge portion 128 and an upper (outflow or downstream) edge portion 130 defining a plurality of alternating projections 132 and notches 134, or castellations, that generally follow the shape of a row of struts of the frame 12. The inflow and outflow edge portions 128, 130 can have other shapes in alternative examples. For example, in one implementation, the inflow edge portion 128 can be formed with a plurality of projections generally conforming to the shape of a row of struts of the frame 12, while the outflow edge portion 130 can be straight.

The outer skirt 18 may comprise an inner side 136 (e.g., FIGS. 22-24) opposite an outer side 138 (e.g., FIGS. 21-24), where the inner side 136 is configured to face radially inward (towards the lumen of the valve 10) while the outer side 138 faces radially outward (towards the exterior of the valve and the surrounding native tissue). Specifically, the outer skirt 18 may be mounted on an outer side 140 of the frame 12 such that the inner side 136 of the outer skirt 18 faces and directly contacts the outer side 140 of the frame 12. In particular examples, the outer side 138 can comprise a soft, plush material so as to cushion and seal against native tissues surrounding the prosthetic valve 10. In certain examples, the outer skirt 18 can be made from any of a variety of woven, knitted, or crocheted fabrics wherein the surface of the outer side 138 is a plush nap or pile of the fabric. Exemplary fabrics having a pile include velour, velvet, velveteen, corduroy, terrycloth, fleece, etc.

In alternative examples, the outer skirt 18 be made of a non-woven fabric such as felt, or fibers such as non-woven cotton fibers. The outer skirt 18 can also be made of porous or spongey materials such as, for example, any of a variety of compliant polymeric foam materials, or woven fabrics, such as woven PET.

As shown in FIG. 1, the outflow edge portion 130 (e.g., projections 132) of the outer skirt 18 can be attached and/or otherwise secured to the third row of angled struts 40 (FIG. 5) of the frame 12. The projections 132 can, for example, be wrapped over the struts of the third row of angled struts 40 and secured with sutures 146. Thus, in such examples, an outflow end 142 of the outer skirt 18 may be positioned more proximate the inflow end 22 of the frame 12 than the outflow end 82 of the inner skirt 17. However, in other examples, such as is shown in FIG. 29, the outflow edge portion 130 of the outer skirt 18 and the outflow edge portion 68 of the inner skirt 17 may be secured to the frame 12 at the same axial position on the frame 12 with a single set of sutures that extends all of the way through the frame 12 and the skirts 17, 18. For example, as shown in FIG. 29, the sutures 70 can be omitted and the sutures 146 can instead extend all of the way through the frame 12 and both of the skirts 17, 18, to secure the outflow edge portions 68, 130 of the inner and outer skirts 17, 18, respectively, to the frame 12 at the same axial position on the frame 12, such as to the third row of angled struts 40.

The outer skirt 18 can additionally or alternatively be secured to the frame at the first row of angled struts 36 and/or the second row of angled struts 38. In some examples, an inflow end 144 of the outer skirt 18 may extend to, but not past, the apices 62 at the inflow end 22 of the frame 12. However, in other examples, the inflow end 144 of the outer skirt 18 may extend past the apices 62 at the inflow end of the frame 12. In still further examples, the inflow end 144 of the outer skirt 18 may not extend to the apices 62 at the inflow end 22 of the frame 12 and may stop short of the apices 62 at the inflow end of the frame 12. For example, the outer skirt 18 need not extend all the way to the inflow end 22 of the frame 12, and instead the inflow end 144 of the outer skirt 18 can secured to another location on the frame 12, such as to the second row of angled struts 38.

The height of the outer skirt 18 (as measured from the inflow end 144 to the outflow end 142) can vary in alternative examples. For example, in some examples, the outer skirt 18 can cover the entire outer surface of the frame 12, with the inflow edge portion 128 secured to the inflow end 22 of the frame 12 and the outflow edge portion 130 secured to the outflow end 24 of the frame 12. In another example, the outer skirt 18 can extend from the inflow end 22 of the frame 12 to the second row of angled struts 38, or to the fourth row of angled struts 42, or to a location along the frame 12 between two rows of struts.

The outer skirt 18 desirably is sized and shaped relative to the frame 12 such that when the prosthetic valve 10 is in its radially expanded state (e.g., FIGS. 1 and 3), the outer skirt 18 fits snugly (in a tight-fitting manner) against the outer side 140 of the frame 12. When the prosthetic valve 10 is crimped to the radially compressed state (FIG. 2) for delivery, the portion of the frame on which the outer skirt is mounted can axially elongate. The outer skirt 18 desirably has sufficient elasticity to stretch in the axial direction upon radial compression of the frame so that it does not to prevent full radial compression of the frame or deform the struts during the crimping process.

In some examples, the inner skirt 17 and/or the outer skirt 18 (e.g., the inflow edge portion 66 of the inner skirt 17 and/or the inflow edge portion 128 of the outer skirt 18) may additionally be sutured to the frame 12 at or near the inflow end 22 of the frame, such as to the first row of angled struts 36. For example, as shown in FIG. 29, the inflow edge portions 66, 128 of both the inner and outer skirts 17, 18, respectively, may be coupled to the frame 12 at or near the inflow end 22 of the frame 12 (e.g., to the first row of angled struts 36) via sutures 320. The sutures 320 can extend all of the way through the frame 12 and the skirts 17, 18 to secure the inflow edge portions 66, 128 of the skirts 17, 18, respectively, to the frame 12, as shown in FIG. 29. However, in other examples, the sutures 320 can extend through the frame 12 and only one of the skirts 17, such as only the inner skirt 17, to secure only the inflow edge portion 66 of the inner skirt 17 to the frame 12. Alternatively, the sutures 320 can extend through the frame 12 and only the outer skirt 18 to secure only the inflow edge portion 128 of the outer skirt 18 to the frame 12.

In some examples, as shown in FIG. 29, the outer skirt 18 may be oversized relative to the frame 12 to accommodate for the axial elongation of the frame 12 during crimping or other radial compression. Specifically, the portion of the outer skirt 18 included between the sutures 146 and the sutures 320 may be longer than the corresponding region of the frame 12 (i.e., the portion of the frame included between the sutures 146 and the sutures 320) when the frame 12 is in the radially expanded state. The slack created by the oversized outer skirt 18 helps the outer skirt 18 accommodate the extra axial elongation of the frame 12 during radial compression of the frame 12. In some examples, because the outer skirt 18 is longer than the frame 12 in this region of the frame 12 (when the frame is in the radially expanded state), the outer skirt 18 can include a bunched or pleated portion 330 when the frame 12 is in the radially expanded state. The bunched portion 330 unfurls and flatten as the frame 12 is radially compressed and allows the outer skirt 18 to lie flatter against the frame 12 in the radially expanded state. Thus, both the bunched portion 330 of the outer skirt 18 and the frame 12 can axially elongate when the frame 12 is radially compressed, such as during crimping. In some examples, the bunched portion 330 can be formed by folding the outer skirt 18, such as in a zigzag pattern having a plurality of circumferentially extending folds. In some examples, the inner skirt 17 can additionally or alternatively include a similar bunched portion to facilitate the radial compression and axial elongation of the frame 12. Additionally, the bunched portion can be formed in the outer skirt and/or inner skirt in any of the examples shown in FIGS. 22-24.

However, in other examples, the inner skirt 17 and/or the outer skirt 18 may only be sutured to the frame 12 at their outflow edge portions 68, 130, respectively, and may hang loosely at their inflow edge portions 66, 128, respectively to facilitate movement (e.g., axial elongation) of the apices 62 at the inflow end 22 of the frame 22 relative to the skirt assembly 16.

The inflow edge portions 66, 128 of the inner and outer skirts 17, 18, respectively, may be stitched together via sutures or stitches 150 proximate the inflow end 22 of the frame 12 to form the pocket 20 at the inflow end 22 of the frame 12. In the examples shown in FIGS. 22-24, the sutures 150 may only extend through each of the skirts 17, 18. In some such examples another suture (e.g., suture 320 shown in FIG. 29) located proximate to the sutures 150 can extend through the frame 12 and one or both of the skirts 17, 18 to secure the skirts 17, 18 to the inflow end 22 of the frame 12. For example, as shown in FIG. 29, the inflow edge portions 66 and/or 128 of the inner and/or outer skirts 17, 18, respectively, can be sutured to the frame 12 to the frame first via the sutures 320. Then, the inflow edge portions 66, 128 of the skirts 17, 18 can be sutured together via a separate set of sutures, such as sutures 150 (FIGS. 22-24), or a separate skirt (e.g., skirt 302 shown in FIG. 28) can be sutured to the inflow edge portions 66, 128 of the inner and outer skirt 17, 18, respectively.

In another example, and as shown in FIG. 29, the inflow edge portions 66 and/or 128 of the inner and/or outer skirts 17, 18, respectively, can be sutured to the frame 12 via the sutures 320 such that a portion of the inner skirt 17 extends beyond the inflow end 22 of the frame 12. This extended or dangling portion of the inner skirt 17 can be of sufficient length to form the pocket 20 and can be wrapped around the inflow end 22 of the frame 12 and sutured to the inflow edge portion 128 of the outer skirt 18 (at or near the sutures 320) with sutures 150 to form the pocket 20.

In the examples shown in FIGS. 22-24, the inner skirt 17 and/or the outer skirt 18 may extend past the apices 62 at the inflow end 22 of the frame 12 when the frame 12 is in the radially expanded state, such that the pocket 20 creates room between (and separates) the inflow end 22 of the frame 12 (including the apices 62) and the skirt assembly 16. As such, the apices 62 are positioned within the pocket 20 and may be spaced away from the skirt assembly 16 when the frame 12 is in the radially expanded state. The pocket 20 also may extend circumferentially around the inflow end 22 of the frame 12, such that all of the apices 62 at the inflow end 22 of the frame 12 are positioned within the pocket 20.

The pocket 20 has an inflow end 154 (i.e., the section/portion of the pocket 20 that is positioned axially farthest from the inflow end 22 of the frame 12) that may extend circumferentially around the inflow end 22 of the frame 12. Thus, the pocket 20 extends axially a distance Y between the apices 62 at the inflow end 22 of the frame 12 and the skirt assembly 16 when the frame 12 is in the radially expanded state. That is, the pocket 20 can separate the apices 62 at the inflow end 22 of the frame 12 from the skirt assembly 16 by the distance Y. Thus, the inflow end 22 of the frame 12 (including the apices 62) can be spaced axially away from the skirt assembly 16 at the inflow end 154 of the pocket 20 by the distance Y when the frame 12 is in the radially expanded state. In particular examples, when the frame is in the radially expanded state, the axial length of the pocket 20 (i.e., the distance Y between apices 62 at the inflow end of the frame 12 and the inflow end 154 of the pocket 20) may be at least 0.1 mm, at least 0.2 mm, at least 0.3 mm, at least 0.4 mm, at least 0.5 mm, at least 0.6 mm, at least 0.7 mm, at least 0.8 mm, at least 0.9 mm, at least 1.0 mm, at least 1.2 mm, at least 1.5 mm, at least 2.0 mm, at most 5.0 mm, at most 4.0 mm, at most 3.0 mm, at most 2.5, at most 2.0, at most 1.5, and/or at most 1.0 mm.

As the frame 12 is radially compressed both the entire skirt assembly 16 (the entirety of the skirts 17, 18, and/or 302) and the frame 12 may axially elongate, although the frame 12 may axially elongate more than the skirt assembly 16. However, the pocket 20 compensates for the additional elongation of the frame and can prevent the apices 62 from the protruding through the skirt assembly when the prosthetic valve is radially compressed to the radially compressed state.

In some examples, when the frame 12 is in the radially compressed state, the length Y of the pocket 20 can be zero (i.e., the pocket 20 can disappear completely when the frame 12 is in the radially compressed state), such that the apices 62 of the frame 12 directly contact the skirt assembly 16. However, even in examples where the apices 62 directly contact the skirt assembly 16, they still do not protrude through the skirt assembly 16. In some examples, the skirt assembly 16 can be resilient and can stretch when the apices 62 contact and push on the skirt assembly 16. This ability to stretch allows the skirt assembly 16 to accommodate even more axial elongation of the frame 12 when the apices 62 directly contact the skirt assembly 16. In some examples, one or more apices 62 may protrude slightly through the skirt assembly 16 at the pocket, but the majority of the apices 62 are still completely covered by the skirt assembly within the pocket.

In other examples, the pocket 20 can still exist even when the frame 12 is in the radially compressed state, and the apices 62 of the frame 12 can still be physically separated from the inflow end 154 of the pocket 20 (i.e., the apices 62 may not directly contact the skirt assembly 16 even in the radially compressed state and the distance Y is greater than zero). When present, the pocket 20 itself may be hollow and/or may contain only air.

In one example, (FIGS. 22, and 26A-27B) the inner skirt 17 may form the pocket 20. In such examples, the outer skirt 18 may not extend past the inflow end 22 of the frame 12 (i.e., the outer skirt 18 may extend to, or short of, the inflow end 22 of the frame 12), and instead the inner skirt 17 may extend past the inflow end 22 of the frame 12, wrap around the apices 62 of at the inflow end 22 of the frame 12, and form the pocket 20. Specifically, the inner skirt 17 may extend past the inflow end 22 of the frame 12, fold back over itself at the inflow end 154 of the pocket 20 such that the crease and/or fold line (i.e., vertex) of the inner skirt 17 (the point at which the inner skirt 17 folds back over itself) forms and/or defines the inflow end 154 of the pocket 20, and may terminate at the inflow edge portion 128 of the outer skirt 18. In some examples, such as is shown in FIG. 22, the inflow edge portion 66 of the inner skirt 17 may overlap the inflow edge portion 128 of the outer skirt 18 such that the inflow edge portion 66 of the inner skirt 17 directly contacts and/or covers the outer side 138 of the outer skirt 18. In other examples, the inner and outer skirts 17, 18 may not overlap with one another, and instead the inflow ends 84, 144 of the inner and outer skirts 17, 18, respectively, may directly abut one another and/or be positioned adjacent to one another. Also, in other examples, the outer skirt 18 may extend beyond the apices 62 at the inflow end of the frame, but is shorter than the inner skirt 17, which forms the majority of the pocket 20. For example, the outer skirt 18 can extend beyond the apices 62 at the inflow end of the frame to a location between the apices 62 and the inflow end 154 of the pocket 20.

In some such examples, the inflow edge portion 66 of the inner skirt 17 may extend over and/or cover the outer side 140 of the frame 12. Specifically, the outer skirt 18 may be positioned on the outer side 140 of the frame 12 such that the inner side 136 of the outer skirt 18 directly contacts the outer side 140 of the frame 12, and the inflow edge portion 66 of the inner skirt 17 may extend over and/or directly contact the outer side 138 of the outer skirt 18, such that the inflow edge portion 128 of the outer skirt 18 is positioned between the frame 12 and the inflow edge portion 66 of the inner skirt 17. However, in other examples, the inflow edge portion 66 of the inner skirt 17 may extend from the inflow end 154 of the pocket 20 towards and/or to the apices 62, but may not extend past the apices 62 on the outside of the frame, and as such, may not cover the outer side 140 of the frame 12. In such examples, the inner skirt 17 may still entirely form the pocket 20, but the inflow end 84 of the inner skirt 17 and the inflow end 144 of the outer skirt 18 may abut one another (without the inner skirt overlapping the outer skirt) at the inflow end 22 of the frame 12 such that the inner skirt 17 does not extend over the outer side 140 of the frame 12.

Figure 26A:
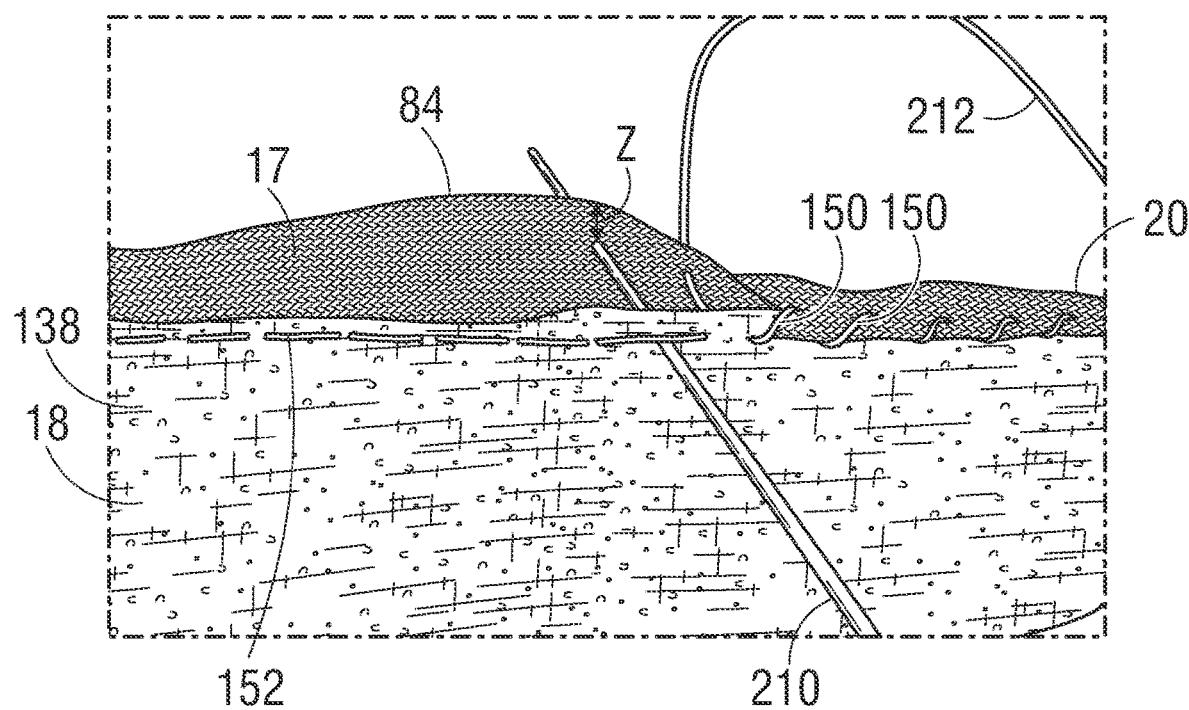
FIG. 26A illustrates an exterior side perspective view of an outflow edge portion of the inner skirt of FIGS. 11-15 and 20 aligned on the frame shown in FIGS. 4-10 and 20 of the prosthetic heart valve shown in FIGS. 1-3.
Figure 26B:
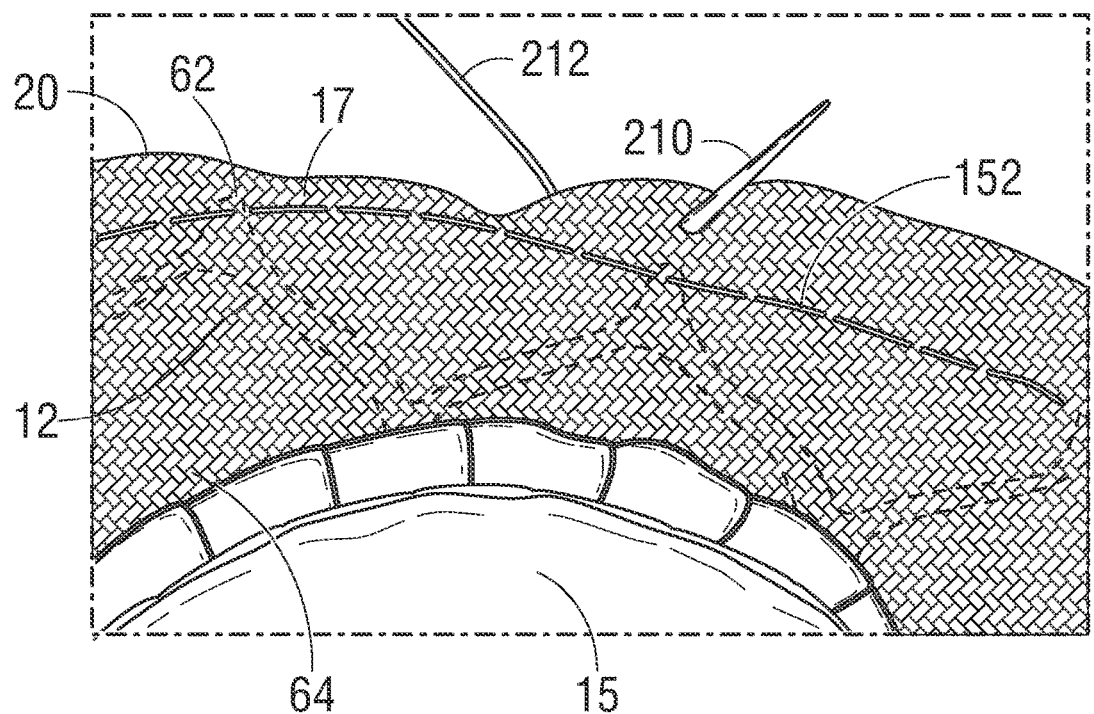
FIG. 26B illustrates an enlarged view of the outflow edge portion of the inner skirt shown in FIG. 26A.

FIGS. 26A-26B show one method of assembling the inner and outer skirts together on the frame to form the pocket 20 configuration of FIG. 22. The inner skirt 17 and the outer skirt 18 can be stitched together with a plurality of in-and-out stitches 152 along a stitch line spaced from the edges of the skirts 17, 18 at or slightly above the apices 62 at the inflow end of the frame 12. As shown in FIGS. 26A-26B, to form the pocket 20, the assembler may pierce the outer skirt 18 with a threading needle 210 just below the stitches 152 (with the valve turned upside down) from the outer side 138 to the inner side 136 of the outer skirt 18, and then pierce the inner skirt 17 from the outer side 65 to the inner side 64 of the inner skirt 17. The assembler may then wrap the thread 212 over the inflow end 84 of the inner skirt 17, pulling and folding the inflow end portion 66 of the inner skirt 17 over the inflow edge portion 128 of the outer skirt 18, and pressing the outer side 65 of the inner skirt 17 against the outer side 138 of the outer skirt 18. The assembler may then pierce the outer skirt 18 again at a circumferentially spaced position from the previous insertion point to complete a whip stitch 150 and start another stitch 150.

To ensure that proper pocket length (e.g., distance Y) is maintained when stitching the inner and outer skirts 17, 18 together, a user may stitch the inner skirt 17 at least a threshold distance Z (FIG. 26A) from the inflow end 84 of the inner skirt 17. That is, when piercing the inner skirt 17 with the threading needle 210 to form the stitches 150 with thread 212, the user may maintain the threshold distance Z (FIG. 26A) between the threading needle 210 and the inflow end 84 of the inner skirt 17. The threshold distance Z may be at least at least 0.1 mm, at least 0.2 mm, at least 0.3 mm, at least 0.4 mm, at least 0.5 mm, at least 0.6 mm, and/or at least 0.7 mm.

Figure 27A:
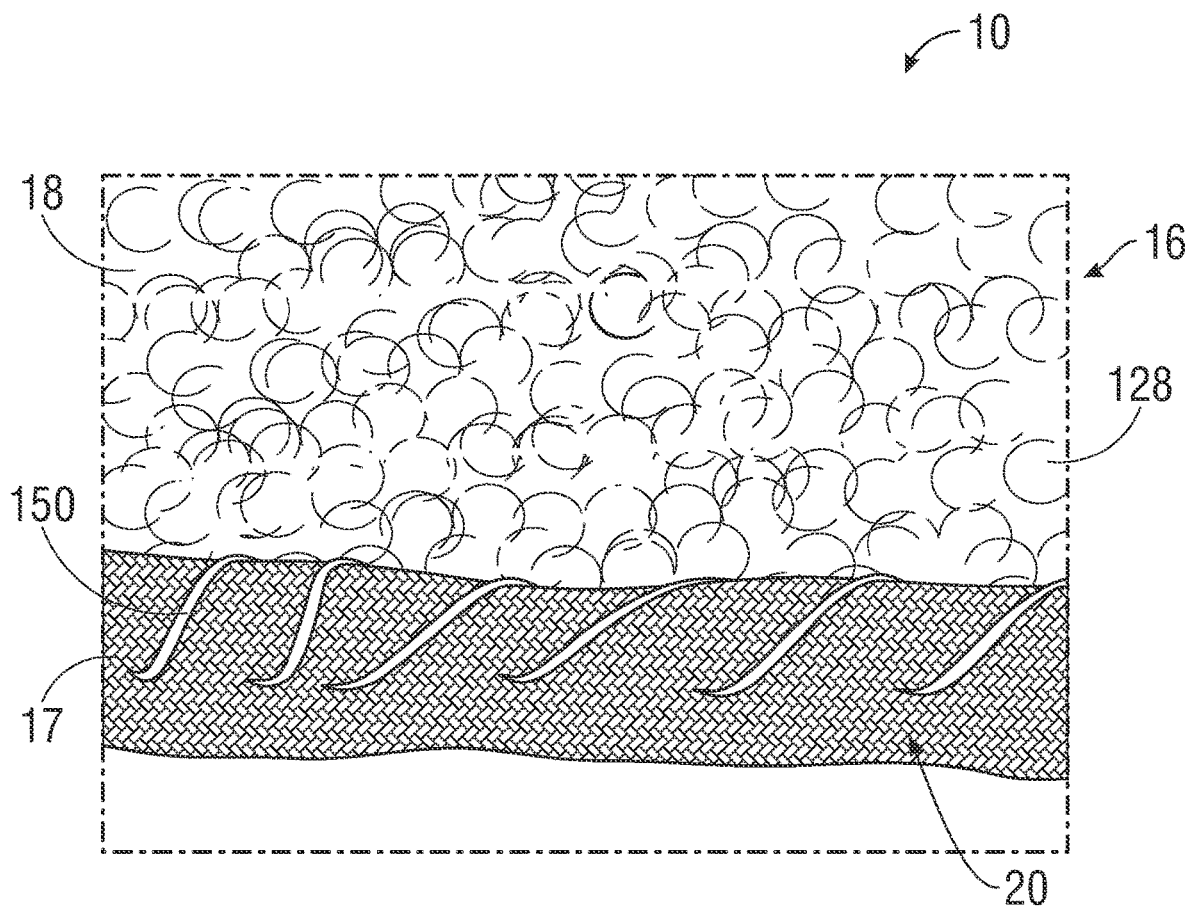
FIG. 27A illustrates an exterior perspective view of inflow edge portions of the inner and outer skirts shown in FIGS. 11-15 and 20-21.
Figure 27B:
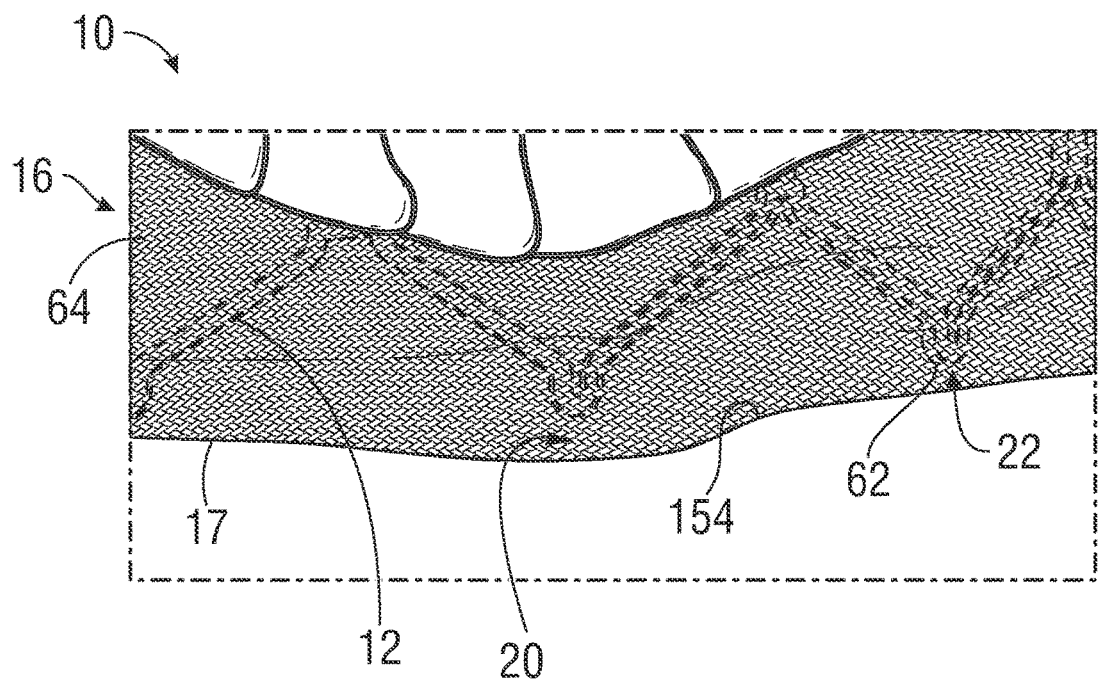
FIG. 27B illustrates an interior perspective view of the inflow edge portions of the skirts shown in FIG. 27A.
Figure 28:
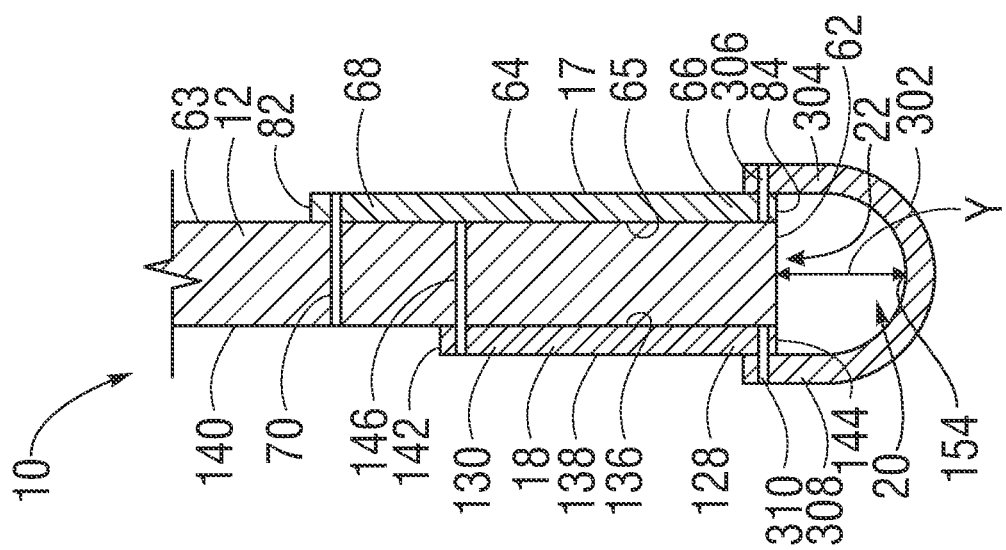
FIG. 28 illustrates a cross sectional view of an inflow edge portion of the prosthetic heart valve shown in FIGS. 1-3 in the radially expanded state shown in FIG. 3, according to an example.

FIGS. 27A-27B show the fully formed and completed pocket 20 after the inner and outer skirts 17, 18 have been stitched together (FIG. 27A shows the outer side of the valve 10 and FIG. 27B shows the inner side of the valve 10). As shown in FIGS. 27A-27B, the skirt assembly 16 extends below the apices 62 at the inflow end 22 of the frame 12 to create the pocket 20. In the particular example shown in FIGS. 27A-27B, the inner skirt 17 forms the pocket 20. The inner skirt 17 wraps around the apices 62, over the outer skirt 18, and is stitched to the outer skirt 18 at the inflow edge portion 128 of the outer skirt 18. Specifically, the inner skirt 17 extends below the apices 62 at the inflow end 22 of the frame 12, folds over itself at the inflow end 154 of the pocket 20, extends up and over the outer skirt 18 on the outer side 140 of the frame 12, and is stitched to the outer skirt 18 with stitches 150 to create the pocket 20. The pocket 20 may extend circumferentially around the entire inflow end 22 of the frame 12 so that all of the apices 62 are fully covered by the skirt assembly 16 in both the radially expanded and the radially compressed (i.e., crimped) states.

The pocket 20 provides extra space/room between the apices 62 and the skirt assembly 16 so that the apices 62 do not protrude through the skirt assembly 16 when the frame 12 is crimped. That is, the pocket 20 allows the frame 12 to axially lengthen when radially compressed and ensures that the apices 62 are still fully covered by the skirt assembly 16 when the frame 12 is in the radially compressed (i.e., crimped) state. Preventing the apices 62 from protruding through the skirt assembly during crimping and keeping them covered by the skirt assembly 16 even in the crimped state provides several advantages. First, it helps prevent the apices 62 from contacting the introducer sheath, thereby reducing the push force needed to push the prosthetic valve 10 through the introducer sheath and protecting against damage to the apices. Second it can protect against the apices contacting and causing trauma to the surrounding tissue as the prosthetic valve (while crimped on a delivery apparatus) is advanced through the patient's vasculature.

In another example, (FIG. 24) the outer skirt 18 may form the pocket 20. In such examples, the inner skirt 17 may not extend past the inflow end 22 of the frame 12 (i.e., the inner skirt 17 may extend to, or short of, the inflow end 22 of the frame 12), and instead the outer skirt 18 may extend past the inflow end 22 of the frame 12, wrap around the apices 62 of at the inflow end 22 of the frame 12, and form the pocket 20. Specifically, the outer skirt 18 may extend past the inflow end 22 of the frame 12, fold back over itself at the inflow end 154 of the pocket 20 such that the crease and/or fold line (i.e., vertex) of the outer skirt 18 (the point at which the outer skirt 18 folds back over itself) forms and/or defines the inflow end 154 of the pocket 20, and may terminate at the inflow edge portion 66 of the inner skirt 17. In some examples, such as is shown in FIG. 24, the inflow edge portion 128 of the outer skirt 18 may overlap with the inflow edge portion 66 of the inner skirt 17 such that the inflow edge portion 128 of the outer skirt 18 directly contacts and/or covers the inner side 64 of the inner skirt 17. In other examples, the inner and outer skirts 17, 18 may not overlap with one another, and instead the inflow ends 84, 144 of the inner and outer skirts 17, 18, respectively, may directly abut one another and/or be positioned adjacent to one another. Also, in other examples, the inner skirt 17 may extend beyond the apices 62 at the inflow end of the frame, but is shorter than the outer skirt 18, which forms the majority of the pocket 20. For example, the inner skirt 17 can extend beyond the apices 62 at the inflow end of the frame to a location between the apices 62 and the inflow end 154 of the pocket 20.

In some examples such, the inflow edge portion 128 of the outer skirt 18 may extend over and/or cover the inner side 63 of the frame 12. Specifically, the inner skirt 17 may be positioned on the inner side 63 of the frame 12 such that the outer side 65 of the inner skirt 17 directly contacts the inner side 63 of the frame 12, and the inflow edge portion 128 of the outer skirt 18 may extend over and/or directly contact the inner side 64 of the inner skirt 17, such that the inflow edge portion 66 of the inner skirt 17 is positioned between the frame 12 and the inflow edge portion 128 of the outer skirt 18. However, in other examples, the inflow edge portion 128 of the outer skirt 18 may extend from the inflow end 154 of the pocket 20 towards and/or to the apices 62, but may not extend past the apices 62, and as such, may not cover the inner side 63 of the frame 12. In such examples, the outer skirt 18 may still entirely form the pocket 20, but the inner skirt 17 and the outer skirt 18 may abut one another at the inflow end 22 of the frame 12 such that the outer skirt 18 does not extend over the inner side 63 of the frame 12.

In yet another example, both the inner and outer skirts 17, 18 may form the pocket 20. In such examples, the inner skirt 17 and the outer skirt 18 may extend past the inflow end 22 of the frame 12 and may be stitched together at a position below the inflow end 22 of the frame 12 (e.g., below the apices 62 at the inflow end 22 of the frame 12). In some such examples, (FIG. 23) the inner and outer skirts 17, 18 may be stitched together at the inflow end 154 of the pocket 20, such that the inflow ends 84, 144 of the inner and outer skirt 17, 18, respectively, form the inflow end 154 of the pocket 20. In such examples, the inner and outer skirts 17, 18 may extend below the inflow end 22 of the frame 12 by approximately the same amount (e.g., the distance Y). In some examples (FIG. 23), the inflow ends 84, 144 of the inner and outer skirt 17, 18, respectively, may directly abut one another and may not overlap with one another. However, in other examples, the skirts 17, 18 may overlap with one another at the pocket 20.

In yet further examples, such as is shown in FIGS. 28 and 30-31, the skirt assembly 16 can include a third skirt 302 (which also may be referred to herein as "pocket skirt 302") that can be coupled to the inner skirt 17, the outer skirt 18, and/or the frame 12 to form at least a portion of the pocket 20 when the frame 12 is in the radially expanded state. For example, in the example shown in FIG. 28, a first end portion 304 of the third skirt 302 can overlap with and be coupled (e.g., stitched) to the inflow end portion 66 of the inner skirt 17, such as via sutures 306, and an opposite second end portion 308 of the third skirt 302 can overlap with and be coupled (e.g., stitched) to inflow edge portion 128 of the outer skirt 18, such as via sutures 310. Because the third skirt 302 may be significantly longer than the width of the frame 12 and the skirts 17, 18, the third skirt 302 may extend beyond the inflow end of the frame 12 (off the inner and outer skirts 17, 18) when the frame 12 is in the radially expanded state, thereby forming the pocket 20.

As another example, as shown in FIG. 30, instead of overlapping with and being coupled (e.g., stitched) to the inner and outer skirts 17, 18, the third skirt 302 can instead be stitched to itself and/or the frame 12 and can abut the inner and outer skirts 17, 18 at or near the inflow end 22 of the frame 12. Specifically, the first end portion 304 of the third skirt 302 can abut the inflow end 84 of the inner skirt 17 and/or the second end portion 308 of the third skirt 302 can abut the inflow end 144 of the outer skirt 18. Further, the first and second end portions 302, 308 of the third skirt 302 can be coupled (e.g., stitched) together, such as via sutures 322 that can extend circumferentially around the frame 12. In some such examples, the sutures 322 can extend through openings in the frame 12, such through the first row of open cells 54 (FIG. 5). In other examples, the first and second end portions 302, 308 of the third skirt 302 can be stitched directly to the frame 12, such as directly to the first row of angled struts 36 (FIG. 5). In either of the above examples, the third skirt 302 can effectively hang off the first row of angled struts 36 and/or apices 62 of the frame 12 at the inflow end 22 of the frame 12, and can extend beyond the inflow end 22 of the frame 12 to form the pocket 20.

In any of the above examples where the third skirt 302 is coupled (e.g., stitched) to the skirts 17, 18 to form at least a portion of the pocket 20, one or both of the skirts 17, 18 also can form at least a portion of the pocket 20. That is, one or both of the skirt 17, 18 need not stop at, or short of, the inflow end 22 of the frame 12 as depicted in FIGS. 28 and 30, and instead one or both of the skirts 17, 18 can extend beyond the inflow end 22 of the frame 12 to form at least a portion of the pocket 20. In other examples however, both of the skirts 17, 18 can stop at, or short of, the inflow end 22 of the frame 12 (such that the skirts 17, 18 do not extend beyond the inflow end of the frame 12) and the third skirt 302 alone can form the entire pocket 20.

As yet another example, one or both of the skirts 17, 18 can wrap around the outside of the third skirt 302. For example, as shown in FIG. 31, the inner skirt 17 can wrap all of the way around the third skirt 302 (such that it hugs and/or otherwise contacts the outer side of the third skirt 302) over the outer side 138 of the outer skirt 18 and can be coupled (e.g., stitched) to the outer skirt 18, such as via sutures 150. In another example, the outer skirt 18 can instead wrap all of the way around the third skirt 302 (such that it hugs and/or otherwise contacts the outer side of the third skirt 302) over the inner side 64 of the inner skirt 17 and can be coupled (e.g., stitched) to the inner skirt 17, such as via sutures 150. In yet further examples, both of the skirts 17, 18 can extend around the third skirt 302 and can be coupled (e.g., stitched) together at a position where the skirts 17, 18 overlap with the third skirt 302, such as a position below the inflow end 22 of the frame 12.

Although the inner and outer skirts 17, 18 are shown and described as being secured to one another at the inflow edge portions 66, 128, respectively via stitches 150, it should be appreciated that the inflow edge portions 66, 128 may be attached to one another using additional and/or alternative coupling means, such as ultrasonic welding, adhesives, mechanical fasteners, etc.

Further, although the pocket 20 is shown and described as being formed/included at the inflow end 22 of the frame 12, it should be appreciated that the pocket 20 may additionally or alternatively be included/formed at the outflow end 24 of the frame 12. Specifically, the inner and/or outer skirts 17, 18 may extend to and/or past the outflow end 24 of the frame 12 and may be stitched together at or near the outflow end 24 of the frame 12 in a similar manner to that described above for the inflow end 22 of the frame 12 to form the pocket 20 (e.g., as shown in FIGS. 22-24) at the outflow end 24 of the frame 12. In some such examples, the pocket 20 may be formed at both the inflow end 22 and the outflow end 24 of the frame 12 so that the valve 10 includes two of the pockets 20, one at each end of the frame 12. In other such examples, the pocket 20 may be formed at the only the outflow end 24 of the frame 12 instead of the inflow end 22 of the frame 12.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly positioned within and coupled to the frame, wherein the leaflet assembly comprises a plurality of leaflets positioned entirely within the frame;
a skirt assembly comprising:
an inner skirt that extends circumferentially around an inner side of the frame, wherein the inner skirt has an inflow edge portion and an outflow edge portion; and
an outer skirt that extends circumferentially around an outer side of the frame, wherein the outer skirt has an inflow edge portion and an outflow edge portion,
wherein the inflow edge portion of the outer skirt is stitched to the inflow edge portion of the inner skirt;
wherein the inflow edge portion of the inner skirt and/or the inflow edge portion of the outer skirt form(s) a pocket, wherein the apices are disposed in the pocket, and wherein the pocket has an inflow end; and wherein when the frame is in the radially expanded state, the apices are spaced from the inflow end of the pocket and when the frame is radially compressed from the radially expanded state to the radially compressed state, the apices move closer to the inflow end of the pocket.

Example 2. The prosthetic heart valve of any example herein, particularly example 1, wherein the inflow edge portions of the inner and outer skirts are stitched together at the pocket.

Example 3. The prosthetic heart valve of any example herein, particularly example 2, wherein the inflow edge portions of the inner and outer skirts are stitched together at the inflow end of the pocket.

Example 4. The prosthetic heart valve of any example herein, particularly any one of examples 1-3, wherein the inflow edge portions of the inner and outer skirts extend axially past the inflow end of the frame.

Example 5. The prosthetic heart valve of any example herein, particularly example 4, wherein the inflow edge portions of the inner and outer skirts extend axially approximately the same amount past the inflow end of the frame.

Example 6. The prosthetic heart valve of any example herein, particularly any one of examples 1-5, wherein when the frame is in the radially expanded state, the apices are spaced from the inflow end of the pocket by at least 0.5 mm.

Example 7. The prosthetic heart valve of any example herein, particularly any one of examples 1-6, wherein the pocket extends circumferentially around the inflow end of the frame.

Example 8. The prosthetic heart valve of any example herein, particularly any one of examples 1-7, wherein the outflow edge portion of the inner skirt is stitched to the frame between the inflow and outflow ends of the frame, and wherein the outflow edge portion of the outer skirt is stitched to the frame nearer the inflow end of the frame than the outflow edge portion of the inner skirt.

Example 9. The prosthetic heart valve of any example herein, particularly any one of examples 1-8, wherein the outflow edge portion of the inner skirt comprises a plurality of slits, and wherein the plurality of slits are axially spaced away from a junction of two struts of the frame by at most 0.5 mm.

Example 10. The prosthetic heart valve of any example herein, particularly any one of examples 1-9, wherein the inner skirt contacts the inner side of the frame, and wherein the outer skirt contacts the outer side of the frame.

Example 11. The prosthetic heart valve of any example herein, particularly any one of examples 1-10, wherein the plurality of leaflets do not extend past the inflow end of the frame and are positioned entirely between the inflow and outflow ends of the frame.

Example 12. The prosthetic heart valve of any example herein, particularly any one of examples 1-11, wherein the pocket is hollow.

Example 13. The prosthetic heart valve of any example herein, particularly any one of examples 1 and 6-12, wherein the inner skirt wraps around the apices at the inflow end of the frame, extends over the outer skirt on the outer side of the frame, and forms the pocket.

Example 14. The prosthetic heart valve of any example herein, particularly any one of examples 1 and 6-12, wherein the outer skirt wraps around the apices at the inflow end of the frame, extends over the inner skirt on the inner side of the frame, and forms the pocket.

Example 15. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly comprising a plurality of leaflets, the leaflet assembly positioned within and coupled to the frame;
an outer skirt that extends circumferentially around an outer side of the frame, wherein the outer skirt has an inflow edge portion and an outflow edge portion; and
an inner skirt that extends circumferentially around an inner side of the frame, wherein the inner skirt has an inflow edge portion and an outflow edge portion, wherein the inner skirt folds over itself and forms a pocket at the inflow end of the frame, wherein the apices at the inflow end of the frame are disposed within the pocket, wherein the pocket has an inflow end, and wherein when the frame is in the radially expanded state, the apices are spaced from the inflow end of the pocket and when the frame is radially compressed from the radially expanded state to the radially compressed state, the apices move closer to the inflow end of the pocket.

Example 16. The prosthetic heart valve of any example herein, particularly example 15, wherein the inflow edge portion of the inner skirt is stitched to the inflow edge portion of the outer skirt.

Example 17. The prosthetic heart valve of any example herein, particularly any one of examples 15 or 16, wherein the inner skirt wraps around the plurality of apices at the inflow end of the frame and covers the outer side of the frame.

Example 18. The prosthetic heart valve of any example herein, particularly example 17, wherein the inflow edge portion of the inner skirt extends circumferentially around the outer side of the frame.

Example 19. The prosthetic heart valve of any example herein, particularly any one of examples 15-18, wherein the outer skirt has an inner side opposite an outer side, wherein the inner side of the outer skirt contacts the outer side of the frame, and wherein the inflow edge portion of the inner skirt extends around the inflow end of the frame, over the outer side of the frame, and contacts the outer side of the outer skirt.

Example 20. The prosthetic heart valve of any example herein, particularly any one of examples 15-19, wherein the outer skirt does not extend past the inflow end of the frame.

Example 21. The prosthetic heart valve of any example herein, particularly any one of examples 15-20, wherein when the frame is in the radially expanded state, the apices are spaced from the inflow end of the pocket by at least 0.5 mm.

Example 22. The prosthetic heart valve of any example herein, particularly any one of examples 15-21, wherein the pocket is hollow.

Example 23. The prosthetic heart valve of any example herein, particularly any one of examples 15-22, wherein the outflow edge portion of the inner skirt comprises a plurality of slits, and wherein the plurality of slits are axially spaced away from a junction of two struts of the frame by at most 0.5 mm.

Example 24. The prosthetic heart valve of any example herein, particularly any one of examples 15-23, wherein the plurality of leaflets do not extend past the inflow end of the frame and are positioned entirely between the inflow and outflow ends of the frame.

Example 25. The prosthetic heart valve of any example herein, particularly any one of examples 15-24, further comprising stitching that couples the inflow edge portion of the inner skirt to the inflow edge portion of the outer skirt, wherein the stitching is spaced away from an inflow end of the inner skirt by approximately 0.5 mm.

Example 26. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly comprising a plurality of leaflets, the leaflet assembly positioned within and coupled to the frame;
an inner skirt that extends circumferentially around an inner side of the frame wherein the inner skirt has an inflow edge portion and an outflow edge portion; and
an outer skirt that extends circumferentially around an outer side of the frame, wherein the outer skirt has an inflow edge portion and an outflow edge portion, wherein the outer skirt folds over itself and forms a pocket at the inflow end of the frame, wherein the apices at the inflow end of the frame are disposed within the pocket, wherein the pocket has an inflow end, and wherein when the frame is in the radially expanded state, the apices are spaced from the inflow end of the pocket and when the frame is radially compressed from the radially expanded state to the radially compressed state, the apices move closer to the inflow end of the pocket.

Example 27. The prosthetic heart valve of any example herein, particularly example 26, wherein the inflow edge portion of the outer skirt is stitched to the inflow edge portion of the inner skirt.

Example 28. The prosthetic heart valve of any example herein, particularly any one of examples 26 or 27, wherein the outer skirt wraps around the plurality of apices at the inflow end of the frame and covers the inner side of the frame.

Example 29. The prosthetic heart valve of any example herein, particularly example 28, wherein the inflow edge portion of the outer skirt extends circumferentially around the inner side of the frame.

Example 30. The prosthetic heart valve of any example herein, particularly any one of examples 26-29, wherein the inner skirt has an inner side opposite an outer side, wherein the outer side of the inner skirt contacts the inner side of the frame, and wherein the inflow edge portion of the outer skirt extends around the inflow end of the frame, over the inner side of the frame, and contacts the inner side of the inner skirt.

Example 31. The prosthetic heart valve of any example herein, particularly any one of examples 26-30, wherein the inner skirt does not extend past the inflow end of the frame.

Example 32. The prosthetic heart valve of any example herein, particularly any one of examples 26-31, wherein when the frame is in the radially expanded state, the apices are spaced from the inflow end of the pocket by at least 0.5 mm.

Example 33. The prosthetic heart valve of any example herein, particularly any one of examples 26-32, wherein the pocket is hollow.

Example 34. The prosthetic heart valve of any example herein, particularly any one of examples 26-33, wherein the plurality of leaflets do not extend past the inflow end of the frame and are positioned entirely between the inflow and outflow ends of the frame.

Example 35. The prosthetic heart valve of any example herein, particularly any one of examples 26-34, further comprising stitching that couples the inflow edge portion of the outer skirt to the inflow edge portion of the inner skirt, wherein the stitching is spaced away from an inflow end of the outer skirt by approximately 0.5 mm.

Example 36. A method for assembling a prosthetic heart valve, comprising:
mounting an inner skirt on an inner side of a radially compressible and expandable frame, wherein the frame has an inflow end, and outflow end, and a plurality of apices at the inflow end;
mounting an outer skirt on an outer side of the frame;
mounting a leaflet assembly comprising a plurality of leaflets to the frame such that the leaflet assembly is positioned entirely within the frame, between the inflow and outflow ends of the frame;
stitching the inner skirt and the outer skirt together such that the inner skirt and/or the outer skirt form(s) a pocket at the inflow end of the frame or stitching a third skirt to the inner skirt and the outer skirt such that the third skirt extends beyond the inflow end of the frame and forms the pocket, wherein the plurality of apices are disposed in the pocket, and wherein the pocket has an inflow end that is separated from the plurality of apices of the frame when the frame is in a radially expanded state.

Example 37. The method of any example herein, particularly example 36, wherein the stitching the inner skirt and the outer skirt together comprises stitching the inner and outer skirts together at the pocket such that both the inner and outer skirts form the pocket.

Example 38. The method of any example herein, particularly any one of examples 36 or 37, wherein the stitching the inner skirt and the outer skirt together comprises stitching the inner and outer skirts together at the inflow end of the pocket.

Example 39. The method of any example herein, particularly example 36, further comprising wrapping the inner skirt around the inflow end of the frame over the outer side of the frame such that the inner skirt forms the pocket, and wherein the stitching the inner skirt and the outer skirt together comprises stitching the inner skirt to the outer skirt on the outer side of the frame.

Example 40. The method of any example herein, particularly example 39, wherein the mounting the inner skirt on the frame comprises coupling the inner skirt to the frame such that the inner skirt extends axially past the inflow end of the frame by at least 1.5 mm prior to wrapping the inner skirt around the inflow end of the frame.

Example 41. The method of any example herein, particularly any one of examples 39 or 40, wherein the stitching the inner skirt and the outer skirt together comprises maintaining a distance of approximately 0.5 mm between an inflow end of the inner skirt and the stitches.

Example 42. The method of any example herein, particularly example 36, further comprising wrapping the outer skirt around the inflow end of the frame over the inner side of the frame such that the outer skirt forms the pocket, and wherein the stitching the inner skirt and the outer skirt together comprises stitching the outer skirt to the inner skirt on the inner side of the frame.

Example 43. The method of any example herein, particularly example 42, wherein the mounting the outer skirt on the frame comprises coupling the outer skirt to the frame such that the outer skirt extends axially past the inflow end of the frame by at least 1.5 mm prior to wrapping the outer skirt around the inflow end of the frame.

Example 44. The method of any example herein, particularly any one of examples 42 or 43, wherein the stitching the inner skirt and the outer skirt together comprises maintaining a distance of approximately 0.5 mm between an inflow end of the outer skirt and the stitches.

Example 45. The method of any example herein, particularly any one of examples 36-44, wherein the mounting the inner skirt on the inner side of the frame comprises stitching the inner skirt to a first row of struts on the frame, wherein the mounting the outer skirt on the outer side of the frame comprises stitching the outer skirt to a second row of struts on the frame positioned closer to the inflow end of the frame than the first row of struts.

Example 46. The method of any example herein, particularly example 45, wherein the mounting the inner skirt on the inner side of the frame further comprises aligning an outflow edge portion of the inner skirt with the first row of struts prior to stitching the inner skirt to the first row of struts such that a plurality of slits included on the outflow edge portion of the inner skirt are positioned by at most 0.5 mm from junctions between adjacent struts in the first row of struts.

Example 47. The method of any example herein, particularly example 36, wherein the stitching the third skirt to the inner skirt and the outer skirt comprises stitching a first end portion of the third skirt to an inflow edge portion of the inner skirt and stitching a second end portion of the third skirt to an inflow edge portion of the outer skirt.

Example 48. The method of any example herein, particularly any one of examples 36-47, wherein the inflow end of the pocket is spaced away from the plurality of apices of the frame by at least 0.5 mm when the frame is in the radially expanded state.

Example 49. The method of any example herein, particularly any one of examples 36-48, wherein the pocket is hollow.

Example 50. The method of any example herein, particularly any one of examples 36-49, wherein the pocket extends circumferentially around the inflow end of the frame.

Example 51. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly positioned within and coupled to the frame, wherein the leaflet assembly comprises a plurality of leaflets positioned entirely within the frame;
a skirt assembly comprising:
an inner skirt that extends circumferentially around an inner side of the frame, wherein the inner skirt has an inflow edge portion and an outflow edge portion; and
an outer skirt, separate from the inner skirt, that extends circumferentially around an outer side of the frame, wherein the outer skirt has an inflow edge portion and an outflow edge portion;
wherein the inflow edge portions of the inner skirt and the outer skirt are coupled to each other so as to form a pocket adjacent the inflow end of the frame, wherein the apices are disposed in the pocket, and wherein the pocket has an inflow end; and
wherein when the frame is in the radially expanded state, the apices are spaced from the inflow end of the pocket and when the frame is radially compressed from the radially expanded state to the radially compressed state, the apices move closer to the inflow end of the pocket.

Example 52. The prosthetic heart valve of any example herein, particularly example 51, wherein the inflow edge portions of the inner skirt and the outer skirt extend axially beyond the inflow end of the frame and are stitched together at a location upstream of the inflow end of the frame to form the pocket.

Example 53. The prosthetic heart valve of any example herein, particularly example 51, wherein the inflow edge portion of the inner skirt extends axially beyond the inflow end of the frame, wraps around the apices and is stitched to the outer skirt on the outside of the frame to form the pocket.

Example 54. The prosthetic heart valve of any example herein, particularly example 51, wherein the inflow edge portion of the outer skirt extends axially beyond the inflow end of the frame, wraps around the apices and is stitched to the inner skirt on the inside of the frame to form the pocket.

Example 55. The prosthetic heart valve of any example herein, particularly example 51, wherein the skirt assembly comprises a third skirt, separate from the inner and outer skirts, that extends beyond the inflow end of the frame and forms at least a portion of the pocket.

Example 56. The prosthetic heart valve of any example herein, particularly example 55, wherein the third skirt is stitched to the inflow edge portions of the inner skirt and the outer skirt.

Example 57. The prosthetic heart valve of any example herein, particularly example 55 or 56, wherein the inner skirt and/or the outer skirt extend beyond the inflow end of the frame and also form at least a portion of the pocket, such that the third skirt and the inner skirt and/or the outer skirt form the pocket.

Example 58. The prosthetic heart valve of any example herein, particularly example 55, wherein the third skirt is stitched to itself at a first row of open cells of the frame.

Example 59. The prosthetic heart valve of any example herein, particularly example 55 or 58, wherein the third skirt alone forms the pocket.

Example 60. The prosthetic heart valve of any example herein, particularly any one of examples 51-59, wherein the inner skirt and/or the outer skirt extend around the third skirt.

Example 61. The prosthetic valve of any example herein, particularly any one of examples 51-60, The prosthetic heart valve of any one of claims 51-55, wherein the inner skirt is sutured to the frame at or near the inflow edge portion and at or near the outflow edge portion.

Example 62. The prosthetic valve of any example herein, particularly any one of examples 51-61, wherein the outer skirt is sutured to the frame at or near the inflow edge portion and at or near the outflow edge portion.

Example 63. The prosthetic valve of any example herein, particularly any one of examples 51-62, wherein the inner skirt and the outer skirt are both sutured to a first row of struts of the frame via a first set of sutures and are both sutured to a second row of struts of the frame via a second set of sutures, wherein the first row of struts are positioned more proximate the inflow end of the frame than the second row of struts.

Example 64. The prosthetic valve of any example herein, particularly any one of examples 62 or 63, wherein the outer skirt comprises a bunched portion between the inflow edge portion and the outflow edge portion.

Example 65. The prosthetic valve of any example herein, particularly example 64, wherein the outer skirt is folded in a zigzag pattern in the bunched portion.

Example 66. The prosthetic valve of any example herein, particularly any one of examples 59 or 60, wherein the bunched portion of the outer skirt unfurls and axially elongates when the frame radially compresses Example 67. The prosthetic valve of any example herein, particularly any one of examples 51-66, further comprising the subject matter of any one of examples 1-35.

In view of the many possible examples to which the principles of the disclosed invention may be applied, it should be recognized that the illustrated examples are only preferred examples of the invention and should not be taken as limiting the scope of the invention. Rather, the scope of the invention is defined by the following claims. We therefore claim as our invention all that comes within the scope and spirit of these claims.

The invention claimed is:

1. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly positioned within and coupled to the frame, wherein the leaflet assembly comprises a plurality of leaflets positioned entirely within the frame;
a skirt assembly comprising:
an inner skirt that extends circumferentially around an inner side of the frame, wherein the inner skirt has an inflow edge portion and an outflow edge portion; and
an outer skirt that extends circumferentially around an outer side of the frame, wherein the outer skirt has an inflow edge portion and an outflow edge portion, wherein the inflow edge portion of the outer skirt is stitched to the inflow edge portion of the inner skirt;
wherein the inflow edge portion of the inner skirt and/or the inflow edge portion of the outer skirt form(s) a pocket, wherein the apices are disposed in the pocket, and wherein the pocket has an inflow end; and
wherein when the frame is in the radially expanded state, the apices are spaced from the inflow end of the pocket and when the frame is radially compressed from the radially expanded state to the radially compressed state, the apices move closer to the inflow end of the pocket;
wherein when the frame is in the radially expanded state, the apices are spaced from the inflow end of the pocket by at least 0.5 mm.

2. The prosthetic heart valve of claim 1, wherein the inflow edge portions of the inner and outer skirts are stitched together at the pocket.

3. The prosthetic heart valve of claim 2, wherein the inflow edge portions of the inner and outer skirts are stitched together at the inflow end of the pocket.

4. The prosthetic heart valve of claim 1, wherein the inflow edge portions of the inner and outer skirts extend axially past the inflow end of the frame.

5. The prosthetic heart valve of claim 4, wherein the inflow edge portions of the inner and outer skirts extend axially approximately the same amount past the inflow end of the frame.

6. The prosthetic heart valve of claim 1, wherein the pocket extends circumferentially around the inflow end of the frame.

7. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly positioned within and coupled to the frame, wherein the leaflet assembly comprises a plurality of leaflets positioned entirely within the frame;
a skirt assembly comprising:
an inner skirt that extends circumferentially around an inner side of the frame, wherein the inner skirt has an inflow edge portion and an outflow edge portion; and
an outer skirt that extends circumferentially around an outer side of the frame, wherein the outer skirt has an inflow edge portion and an outflow edge portion, wherein the inflow edge portion of the outer skirt is stitched to the inflow edge portion of the inner skirt;
wherein the inflow edge portion of the inner skirt and/or the inflow edge portion of the outer skirt form(s) a pocket, wherein the apices are disposed in the pocket, and wherein the pocket has an inflow end; and
wherein when the frame is in the radially expanded state, the apices are spaced from the inflow end of the pocket and when the frame is radially compressed from the radially expanded state to the radially compressed state, the apices move closer to the inflow end of the pocket;
wherein the outflow edge portion of the inner skirt is stitched to the frame between the inflow and outflow ends of the frame, and wherein the outflow edge portion of the outer skirt is stitched to the frame nearer the inflow end of the frame than the outflow edge portion of the inner skirt.

8. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly positioned within and coupled to the frame, wherein the leaflet assembly comprises a plurality of leaflets positioned entirely within the frame;
a skirt assembly comprising:
an inner skirt that extends circumferentially around an inner side of the frame, wherein the inner skirt has an inflow edge portion and an outflow edge portion; and
an outer skirt that extends circumferentially around an outer side of the frame, wherein the outer skirt has an inflow edge portion and an outflow edge portion, wherein the inflow edge portion of the outer skirt is stitched to the inflow edge portion of the inner skirt;
wherein the inflow edge portion of the inner skirt and/or the inflow edge portion of the outer skirt form(s) a pocket, wherein the apices are disposed in the pocket, and wherein the pocket has an inflow end; and
wherein when the frame is in the radially expanded state, the apices are spaced from the inflow end of the pocket and when the frame is radially compressed from the radially expanded state to the radially compressed state, the apices move closer to the inflow end of the pocket;
wherein the outflow edge portion of the inner skirt comprises a plurality of slits, and wherein the plurality of slits are axially spaced away from a junction of two struts of the frame by at most 0.5 mm.

9. The prosthetic heart valve of claim 1, wherein the inner skirt contacts the inner side of the frame, and wherein the outer skirt contacts the outer side of the frame.

10. The prosthetic heart valve of claim 1, wherein the plurality of leaflets do not extend past the inflow end of the frame and are positioned entirely between the inflow and outflow ends of the frame.

11. The prosthetic heart valve of claim 1, wherein the pocket is hollow.

12. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly positioned within and coupled to the frame, wherein the leaflet assembly comprises a plurality of leaflets positioned entirely within the frame;
a skirt assembly comprising:
an inner skirt that extends circumferentially around an inner side of the frame, wherein the inner skirt has an inflow edge portion and an outflow edge portion; and
an outer skirt that extends circumferentially around an outer side of the frame, wherein the outer skirt has an inflow edge portion and an outflow edge portion, wherein the inflow edge portion of the outer skirt is stitched to the inflow edge portion of the inner skirt;
wherein the inflow edge portion of the inner skirt and/or the inflow edge portion of the outer skirt form(s) a pocket, wherein the apices are disposed in the pocket, and wherein the pocket has an inflow end; and
wherein when the frame is in the radially expanded state, the apices are spaced from the inflow end of the pocket and when the frame is radially compressed from the radially expanded state to the radially compressed state, the apices move closer to the inflow end of the pocket;
wherein the inner skirt wraps around the apices at the inflow end of the frame, extends over the outer skirt on the outer side of the frame, and forms the pocket.

13. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly positioned within and coupled to the frame, wherein the leaflet assembly comprises a plurality of leaflets positioned entirely within the frame;
a skirt assembly comprising:
an inner skirt that extends circumferentially around an inner side of the frame, wherein the inner skirt has an inflow edge portion and an outflow edge portion; and
an outer skirt that extends circumferentially around an outer side of the frame, wherein the outer skirt has an inflow edge portion and an outflow edge portion, wherein the inflow edge portion of the outer skirt is stitched to the inflow edge portion of the inner skirt;
wherein the inflow edge portion of the inner skirt and/or the inflow edge portion of the outer skirt form(s) a pocket, wherein the apices are disposed in the pocket, and wherein the pocket has an inflow end; and
wherein when the frame is in the radially expanded state, the apices are spaced from the inflow end of the pocket and when the frame is radially compressed from the radially expanded state to the radially compressed state, the apices move closer to the inflow end of the pocket;
wherein the outer skirt wraps around the apices at the inflow end of the frame, extends over the inner skirt on the inner side of the frame, and forms the pocket.

14. A prosthetic heart valve, comprising:
an annular frame comprising an inflow end and an outflow end, wherein the frame is radially compressible and expandable between a radially compressed state and a radially expanded state, wherein the frame comprises a plurality of apices at the inflow end;
a leaflet assembly comprising a plurality of leaflets, the leaflet assembly positioned within and coupled to the frame;
an outer skirt that extends circumferentially around an outer side of the frame, wherein the outer skirt has an inflow edge portion and an outflow edge portion; and
an inner skirt that extends circumferentially around an inner side of the frame, wherein the inner skirt has an inflow edge portion and an outflow edge portion, wherein the inner skirt folds over itself and forms a pocket at the inflow end of the frame, wherein the apices at the inflow end of the frame are disposed within the pocket, wherein the pocket has an inflow end, and wherein when the frame is in the radially expanded state, the apices are spaced from the inflow end of the pocket and when the frame is radially compressed from the radially expanded state to the radially compressed state, the apices move closer to the inflow end of the pocket.

15. The prosthetic heart valve of claim 14, wherein the inflow edge portion of the inner skirt is stitched to the inflow edge portion of the outer skirt.

16. The prosthetic heart valve of claim 14, wherein the inner skirt wraps around the plurality of apices at the inflow end of the frame and covers the outer side of the frame.

17. The prosthetic heart valve of claim 14, wherein the outer skirt has an inner side opposite an outer side, wherein the inner side of the outer skirt contacts the outer side of the frame, and wherein the inflow edge portion of the inner skirt extends around the inflow end of the frame, over the outer side of the frame, and contacts the outer side of the outer skirt.

18. The prosthetic heart valve of claim 14, wherein the outer skirt does not extend past the inflow end of the frame.

19. The prosthetic heart valve of claim 14, wherein when the frame is in the radially expanded state, the apices are spaced from the inflow end of the pocket by at least 0.5 mm.

20. The prosthetic heart valve of claim 14, wherein the plurality of leaflets do not extend past the inflow end of the frame and are positioned entirely between the inflow and outflow ends of the frame.

21. The prosthetic heart valve of claim 14, further comprising stitching that couples the inflow edge portion of the inner skirt to the inflow edge portion of the outer skirt, wherein the stitching is spaced away from an inflow end of the inner skirt by approximately 0.5 mm.

22. A method for assembling a prosthetic heart valve, comprising:
mounting an inner skirt on an inner side of a radially compressible and expandable frame, wherein the frame has an inflow end, and outflow end, and a plurality of apices at the inflow end; mounting an outer skirt on an outer side of the frame;
mounting a leaflet assembly comprising a plurality of leaflets to the frame such that the leaflet assembly is positioned entirely within the frame, between the inflow and outflow ends of the frame;
stitching the inner skirt and the outer skirt together such that the inner skirt and/or the outer skirt form(s) a pocket at the inflow end of the frame or stitching a third skirt to the inner skirt and the outer skirt such that the third skirt extends beyond the inflow end of the frame and forms the pocket, wherein the plurality of apices are disposed in the pocket, and wherein the pocket has an inflow end that is separated from the plurality of apices of the frame when the frame is in a radially expanded state.

23. The method of claim 22, wherein the stitching the inner skirt and the outer skirt together comprises stitching the inner and outer skirts together at the pocket such that both the inner and outer skirts form the pocket.

24. The method of claim 22, wherein the stitching the inner skirt and the outer skirt together comprises stitching the inner and outer skirts together at the inflow end of the pocket.

25. The method of claim 22, further comprising wrapping the inner skirt around the inflow end of the frame over the outer side of the frame such that the inner skirt forms the pocket, and wherein the stitching the inner skirt and the outer skirt together comprises stitching the inner skirt to the outer skirt on the outer side of the frame.

26. The method of claim 25, wherein the mounting the inner skirt on the frame comprises coupling the inner skirt to the frame such that the inner skirt extends axially past the inflow end of the frame by at least 1.5 mm prior to wrapping the inner skirt around the inflow end of the frame.

\* \* \* \* \*